(12) United States Patent
Tomat et al.

(10) Patent No.: US 12,383,518 B2
(45) Date of Patent: *Aug. 12, 2025

(54) DISULFIDE-MASKED PRO-CHELATOR COMPOSITIONS AND METHODS OF USE

(71) Applicant: ARIZONA BOARD OF REGENTS ON BEHALF OF THE UNIVERSITY OF ARIZONA, Tucson, AZ (US)

(72) Inventors: Elisa Tomat, Tucson, AZ (US); Eman A. Akam, Tucson, AZ (US)

(73) Assignee: ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 28 days.

This patent is subject to a terminal disclaimer.

(21) Appl. No.: 17/668,810

(22) Filed: Feb. 10, 2022

(65) Prior Publication Data

US 2022/0175705 A1    Jun. 9, 2022

Related U.S. Application Data

(63) Continuation-in-part of application No. 16/632,217, filed as application No. PCT/US2018/042458 on Jul.
(Continued)

(51) Int. Cl.
*A61K 31/75* (2006.01)
*A61K 31/175* (2006.01)

(52) U.S. Cl.
CPC ................. *A61K 31/175* (2013.01)

(58) Field of Classification Search
CPC .................................................. A61K 31/175
See application file for complete search history.

(56) References Cited

U.S. PATENT DOCUMENTS 5,246,821 A    9/1993    Abe et al.
6,030,846 A    2/2000    Simons et al.
(Continued)

FOREIGN PATENT DOCUMENTS

WO    WO2015200916 A2    12/2015
WO    WO2017112787 A1    6/2017

OTHER PUBLICATIONS

Database Registry Chemical Abstracts Service, Columbus, Ohio, Accession No. RN 1440088-73-2 Entered STN: Jun. 21, 2013.*

(Continued)

*Primary Examiner* — Adam C Milligan
*Assistant Examiner* — Sophia P Hirakis
(74) *Attorney, Agent, or Firm* — NGUYEN TARBET IP LAW

(57) ABSTRACT

Pro-chelator compositions featuring disulfide masks that upon activation yield active chelators. The pro-chelator compositions may be activated intracellularly, for example within cells featuring metal ion dysregulation, cells that proliferate abnormally, etc. The pro-chelators of the present invention include thiosemicarbazones, semicarbazones, and aroyl hydrazones. The pro-chelator compositions of the present invention may be used for a variety of purposes including inhibiting cell proliferation, or treating conditions associated with metal ion dysregulation or abnormal cell proliferation.

11 Claims, 6 Drawing Sheets

Related U.S. Application Data 17, 2018, now abandoned, and a continuation-in-part of application No. 16/200,286, filed on Nov. 26, 2018, now Pat. No. 11,504,346, which is a continuation-in-part of application No. 16/014,905, filed on Jun. 21, 2018, now abandoned, which is a continuation-in-part of application No. PCT/US2016/068061, filed on Dec. 21, 2016, said application No. 16/200,286 is a continuation-in-part of application No. 15/345,393, filed on Nov. 7, 2016, now abandoned, said application No. 16/014,905 is a continuation-in-part of application No. 15/345,393, filed on Nov. 7, 2016, now abandoned, which is a continuation of application No. 14/531,634, filed on Nov. 3, 2014, now Pat. No. 9,486,423.

(60) Provisional application No. 62/533,964, filed on Jul. 18, 2017, provisional application No. 62/270,246, filed on Dec. 21, 2015, provisional application No. 61/899,262, filed on Nov. 3, 2013.

(56) References Cited

U.S. PATENT DOCUMENTS

| | | | |
|---|---|---|---|
| 7,488,747 | B2 | 2/2009 | Fang et al. |
| 7,825,226 | B2 | 11/2010 | Schultz et al. |
| 8,551,976 | B2 | 10/2013 | Franz et al. |
| 8,680,077 | B2 | 3/2014 | Franz et al. |
| 8,685,955 | B2 | 4/2014 | Youdim et al. |
| 9,486,423 | B2 | 11/2016 | Tomat et al. |
| 2006/0252798 | A1 | 11/2006 | Richardson et al. |
| 2012/0276163 | A1 | 11/2012 | Tselepis et al. |
| 2013/0310346 | A1 | 11/2013 | Zurawski |
| 2014/0073645 | A1 | 3/2014 | Linder et al. |
| 2014/0206725 | A1 | 7/2014 | Richardson et al. |
| 2015/0126610 | A1 | 5/2015 | Tomat et al. |
| 2017/0112788 | A1 | 4/2017 | Tomat et al. |

OTHER PUBLICATIONS

"Investigations on Structural and Elctrochemical Properties of some Disulfides Prepared by Schiff Base Reactions" Stephan Kotte, Ingo Jolk, and Bernt Krebs J. Prakt. Chem. 2000, 342, No. 1, (Year: 2000).*

Calvaresi et al., "Glucose conjugation for the specific targeting and treatment of cancer," Chem. Sci. 4, Jun. 1, 2014, 2319-2333.

Younes et al., "Overexpression of the human erythrocyte glucose transporter occurs as a late event in human colorectal carcinogenesis and is associated with an increased incidence of lymph node metastases," Clin. Cancer Res. 2, May 19, 1996, 1151-1154.

Haber et al., "GLUT1 glucose transporter expression in colorectal carcinoma—A marker for poor prognosis," Feb. 2, 1998, Cancer 83, 34-40.

Shen et al., "Overexpression of GLUT1 in colorectal cancer is independently associated with poor prognosis," Int. J. Biol. Markers 26, Jun. 22, 2011, 166-172.

Graziano et al., "Glycolysis gene expression analysis and selective metabolic advantage in the clinical progression of colorectal cancer," Pharmacogenomics J. Mar. 1, 2016, DOI: 10.1038/tpj.2016.13.

Mikata et al., "Metal Complexes of Carbohydrate-targeted Ligands in Medicinal Inorganic Chemistry," Ligand Design In Medicinal Inorganic Chemistry (Storr, T., Ed.) 2014, pp. 145-173, Chapter 6, John Wiley & Sons, Ltd, Chichester, UK.

Liu et al., "Highly water-soluble platinum(II) complexes as GLUT substrates for targeted therapy: improved anticancer efficacy and transporter-mediated cytotoxic properties," Chem. Commun. 49, Feb. 1, 2013, 2421-2423.

Patra et al., "A Potent Glucose-Platinum Conjugate Exploits Glucose Transporters and Preferentially Accumulates in Cancer Cells," Angew. Chem. Int. Ed. 55, 2016, 2550-2554.

Storr et al., "Glycosylated tetrahydrosalens as multifunctional molecules for Alzheimer's therapy," Dalton Trans., Feb. 16, 2009, 3034-3043.

Cao et al., "Targeted Cancer Therapy with a 2-Deoxyglucose-Based Adriamycin Complex," Cancer Res. 73, Feb. 8, 2013, 1362-1373.

Halmos et al., "Synthesis of glucose-chlorambucil derivatives and their recognition by the human GLUT1 glucose transporter," Eur. J. Pharmacol. 318, Oct. 4, 1996, 477-484.

Guenin et al., "Synthesis and Anaphylactogenicity of Monohaptenic Carbohydrate Conjugates," Helv. Chim. Acta 66, 1983, 1101-1109.

Fan et al., "Design, synthesis and biological evaluation of brain-specific glucosyl thiamine disulfide prodrugs of naproxen," Eur. J. Med. Chem. 46, May 20, 2011, 3651-3661.

Cui et al., "Regioselective 6-detrimethylsilylation of per-O-TMS-protected carbohydrates in the presence of ammonium acetate," Tetrahedron Lett. 54, May 18, 2013, 3831-3833.

Jacob et al., "Glucose-aspirin: Synthesis and in vitro anti-cancer activity studies," Bioorg. Med. Chem. Lett. 22, Mar. 23, 2012, 3168-3171.

Peltier-Pain et al., "Warfarin Glycosylation Invokes a Switch from Anticoagulant to Anticancer Activity," ChemMedChem 6, 2011, 1347-1350.

Saaf et al., "Parallels between global transcriptional programs of polarizing caco-2 intestinal epithelial cells in vitro and gene expression programs in normal colon and colon cancer," Mol. Biol. Cell 18, Aug. 8, 2007, 4245-4260.

Harris et al., "Polarized Distribution of Glucose Transporter Isoforms in Caco-2 Cells," Proc. Natl. Acad. Sci. U.S.A. 89, May 18, 1992, 7556-7560.

O'Neil et al., "Uptake of a fluorescent deoxyglucose analog (2-NBDG) in tumor cells," Mol. Imaging Biol. 7, Nov. 12, 2005, 388-392.

Xintaropoulou et al., "A comparative analysis of inhibitors of the glycolysis pathway in breast and ovarian cancer cell line models," Oncotarget 6, Jul. 16, 2015, 25677-25695.

Barnett et al. "Structural Requirements for Binding to Sugar-Transport System of Human Erythrocyte," Biochem. J. 131, Jul. 19, 1972, 211-221.

Lin et al., "Targeting the Delivery of Glycan-Based Paclitaxel Prodrugs to Cancer Cells via Glucose Transporters," J. Med. Chem. 51, May 26, 2008, 7428-7441.

Sun et al. "Iron depletion decreases proliferation and induces apoptosis in a human colonic adenocarcinoma cell line, Caco2," J. Inorg. Biochem. 103, May 20, 2009, 1074-1081.

Lane et al., "Expanding horizons in iron chelation and the treatment of cancer: Role of iron in the regulation of ER stress and the epithelial-mesenchymal transition," BBA Rev. Cancer 1845, Jan. 25, 2014, 166-181.

Whitnall et al., "A class of iron chelators with a wide spectrum of potent antitumor activity that overcomes resistance to chemotherapeutics," Proc. Natl. Acad. Sci. U.S.A. 103, Jun. 15, 2006, 14901-14906.

Medina et al., "Glucose transporters: expression, regulation and cancer," Biol. Res. 35, Feb. 1, 2002, 9-26.

Jung et al., "Improved synthesis of 4-amino-7-nitrobenz-2,1,3-oxadiazoles using NBD fluoride (NBD-F)," Tetrahedron Lett. 52, Mar. 2, 2011, 2533-2535.

Widdison et al., "Semisynthetic maytansine analogues for the targeted treatment of cancer," J. Med. Chem. 49, Mar. 20, 2006, 4392-4408.

Sungaran et al. "Localization and regulation of thrombopoietin mRNa expression in human kidney, liver, bone marrow, and spleen using in situ hybridization." Blood, The Journal of the American Society of Hematology 89.1 (1997): 101-107.

Perez et al. "Iron chelators as potential therapeutic agents for Parkinson's disease." Current bioactive compounds 4.3 (2008): 150-158.

Dayani et al., "Desferoxamine (DFO)-mediated iron chelation: Rationale for a novel approach to therapy for brain cancer," J. Neuro-Oncol. 2004, 67, 367-377.

Nutting et al., "Phase II study of 3-AP Triapine in patients with recurrent or metastatic head and neck squamous cell carcinoma," Ann. Oncol. Dec. 5, 2008, 20, 1275-1279.

(56) References Cited

OTHER PUBLICATIONS

Kontoghiorghes, "Ethical issues and risk/benefit assessment of iron chelation therapy: Advances with Deferiprone/Deferoxamine combinations and concerns about the safety, efficacy and costs of Deferasirox," Hemoglobin 2008, 32, 1-15.
Lee et al., "Direct Fluorescence Monitoring of the Delivery and Cellular Uptake of a Cancer-Targeted RGD Peptide-Appended Naphthalimide Theragnostic Prodrug," J_ Am. Chem. Soc. 2012, 134, 12668-12674.
Wu et al. "In vivo and in situ tracking cancer chemotherapy by highly photostable NIR fluorescent theranostic prodrug." Journal of the American Chemical Society 136.9 (2014): 3579-3588.
Spasojevic et al., "Electrochemical Behavior of the Fe(III) complexes of the Cyclic Hydroxamate Siderophores Alcaligin and Desferrioxamine E," Inorg. Chem. 1999, 38, 449-454.
Bernhardt "Coordination chemistry and biology of chelators for the treatment of iron overload disorders," Dalton Trans. Jun. 18, 2007, 3214-3220.
Ornstein et al., "Iron stimulates urokinase plasminogen activator expression and activates NF-,appa Bin human prostate cancer cells," Nutr. Cancer 2007, 58, 115-126.
Kalinowski et al., "Design, synthesis, and characterization of novel iron chelators: Structure-activity relationships of the 2-benzoylpyridine lhiosemicarbazone series and their 3-nilrobenzoyl analogues as potent antitumor agents," J_ Med. Chem. Apr. 16, 2007, 50, 3716-3729.
Richardson et al., "2-Acetylpyridine Thiosemicarbazones are Potent Iron Chelators and Antiproliferative Agents: Redox Activity, Iron Complexation and Characterization of their Antitumor Activity," J_ Med. Chem. Dec. 15, 2008, 52, 1459-1470.
Choi et al., "Iron intake, oxidative stress-related genes (MnSOD and MPO) and prostate cancer risk in CARET cohort," Carcinogenesis Feb. 22, 2008, 29, 964-970.
Ben-Haim et al. "(18)F-FDG PET and PET/CT in the Evaluation of Cancer Treatment Response," J_ Nucl. Med. Jan. 2009, 50, 88-99.
Liu et al., "Synthesis of 2 '-paclitaxel methyl 2-Glucopyranosyl succinate for specific targeted delivery to cancer cells. Bioorg," Med. Chem. Lett. Nov. 7, 2006, 17, 617-620.
Bensinger et al., "New aspects of the Warburg effect in cancer cell biology," Semin. Cell Dev. Biol. Mar. 8, 2012, 23, 352-361.
Yoshioka et al., "A novel fluorescent derivative of glucose applicable to the assessment of glucose uptake activity of *Escherichia coli*," Biochim. Biophys. Acta 1996, 1289, 5-9.
Heath et al., "Iron Deprivation in Cancer-Potential Therapeutic Implications," Nutrients. Jul. 24, 2013; 5(8): 2836-2859.
Kovacevic et al., "Iron Chelators: Development of Novel Compounds with High and Selective Anti-Tumour Activity," Current Drug Delivery, vol. 7, No. 3, Jul. 2010, pp. 194-207(14).
Buss et al., "Iron chelators in cancer chemotherapy," Curr Top Med Chem. 2004;4(15):1623-35.
Chitambar et al. "Iron-targeting antitumor activity of gallium compounds and novel insights into triapine{®)-meta complexes," Antioxid Redox Signal. Mar. 10, 2013;18(8):956-72.
Yu et al. "The Potent and Novel Thiosemicarbazone Chelators Di-2-pyridylketone-4, 4-dimethyl-3-thiosemicarbazone and 2-Benzoylpyridine-4, 4-dimethyl-3-thiosemicarbazone Affect Crucial Thiel Systems Required or Ribonucleotide Reductase Activity," Molecular Pharmacology Jun. 2011 vol. 79 No. 6 921-931.
Siriwardana et al., "Two cell cycle blocks caused by iron chelation of neuroblastoma cells: separating cell cycle events associated with each block," Physiol Rep. Dec. 1, 2013; 1(7): e00176.
Choi et al. "Effects of oral iron chelator deferasirox on human malignant lymphoma cells," Korean J Hemalol. Sep. 2012; 47(3): 194-201.
Loccufier et al., "Convenient Method for the Preparation of 3-(2-Pyridyl Dilhio) Propionic-Acid N-Hydroxy Succinimide Ester," B Soc Chim Belg. Jul. 10, 1988, 97, 535-539.
Wood et al., "Advances in the Chemistry of Dipyrrins and Their Complexes," Chem. Rev. Apr. 13, 2007, 107, 1831-1861.
Katayev et al. "Dioxygen activation by diiminodipyrromethane complexes of Ni, Pd, and Pt." Inorganic chemistry 46.14 (2007): 5465-5467.
Reid et al. "Tautomerisation and hydrogen-bonding interactions in four-coordinate metal halide and azide complexes of N-donor-extended dipyrromethanes." Dalton Transactions 39.2 (2010): 418-425.
Halper et al. "Heterometallic metal-organic frameworks based on tris (dipyrrinato) coordination complexes." Inorganic chemistry 44.3 (2005): 486-488.
King et al. "Co (III) imidos exhibiting spin crossover and C—H bond activation." Journal of the American Chemical Society 134.43 (2012): 17858-17861.
Hennessy et al. "Complex N-heterocycle synthesis via iron-catalyzed, direct C—H bond amination." Science 340.6132 (2013): 591-595.
Thoi et al. "Diamidodipyrrins: versatile bipyrrolic ligands with multiple metal binding modes." Inorganic chemistry 47.22 (2008): 10533-10541.
Patra, et al. "A thermally stable {FeNO} 8 complex: properties and biological reactivity of reduced MNO systems." Chemical Science 3.2 (2012): 364-369.
Sanders et al."Synthesis, properties, and reactivity of a series of non-heme {FeNO} 7/8 complexes: Implications for Fe-nitroxyl coordination." Journal of inorganic biochemistry 118 (2013): 115-127.
Broring et al. "Preparation, Magnetic and Structural Study on Oxido-Bridged Diiron (III) Complexes with Open-Chain Tetrapyrrolic 2, 2'-Bidipyrrin Ligands." (2009): 3628-3635.
Sessler et al. "Synthesis and Characterization of a Tripyrrane-Copper (II) Complex." Inorganic chemistry 35.23 (1996): 6636-6637.
Bennett et al., "Seeing Red: The Story of Prodigiosin," Adv. Appl. Microbiol. 2000, 47, 1-32.
Furstner, "Chemistry and Biology of Roseophilin and the Prodigiosin Alkaloids: A Survey of the Last 2500 Years," A., Angew. Chem., Int. Ed. 2003, 42, 3582-3603.
D'Alessio et al., "Synthesis and Immunosuppressive Activity of Novel Prodigiosin Derivatives," J_ Med. Chem. Jan. 4, 2000, 43, 2557-2565.
Furstner et al., "Studies on DNA Cleavage by Cytotoxic Pyrrole Alkaloids Reveal the Distinctly Different Behavior of Roseophilin and Prodigiosin Derivatives," ChemBioChem; Feb. 9, 2001, 2, 60-68.
Marchal et al., "Antimicrobial activity of non-natural prodigiosenes," RSC Adv. Oct. 4, 2013, 3, 22967-22971.
Vázquez-Dorbatt et al. "Synthesis of a pyridyl disulfide end-functionalized glycopolymer for conjugation to biomolecules and patterning on gold surfaces." Biomacromolecules 10.8 (2009): 2207-2212.
Calvaresi et al. "Glucose conjugation for the specific targeting and treatment of cancer." Chemical science 4.6 (2013): 2319-2333.
Samukov, "A Simple Preparation of 3-(2-Pyridyldithio)-Propionic Acid," Synthetic Communications, vol. 28, No. 17, 1998. pp. 3213-3217.
Ferlay et al., "Cancer incidence and mortality worldwide: sources, methods and major patterns in GLOBOCAN 2012," Int. J. Cancer 136, Sep. 13, 2014, E359-386.
Bingham et al., "Diet and cancer—the European Prospective Investigation into Cancer and Nutrition," Nat. Rev. Cancer 4, Mar. 2004, 206-215. 10 pages.
Nelson, "Iron and colorectal cancer risk: Human studies," Nutr. Rev. 59, May 2001, 140-148. 9 pages.
Chua et al., "Iron: an emerging factor in colorectal carcinogenesis," World J. Gastroenterol. 16, Feb. 14, 2010, 663-672. 10 pages.
Padmanabhan et al., "Iron and colorectal cancer: evidence from in vitro and animal studies," Nutr. Rev. 73, Apr. 7, 2015, 308-317. 10 pages.
Brookes et al., "Modulation of iron transport proteins in human colorectal carcinogenesis," Gut 55, Apr. 26, 2006, 1449-1460.
Perez et al., "Minding metals: tailoring multifunctional chelating agents for neurodegenerative disease," Dalton Trans. 39, Dec. 17, 2009, 2177-2187.

(56) References Cited

OTHER PUBLICATIONS

Vander Heiden et al., "Targeting cancer metabolism: a therapeutic window opens," Nat. Rev. Drug Discov. 10, Sep. 2011, 671-684.
Akam et al. "Disulfide-masked iron prochelators: Effects on cell death, proliferation, and hemoglobin production." Journal of inorganic biochemistry 180 (2018): 186-193.
Torti et al., "Iron and cancer: more ore to be mined," Nat Rev. Cancer, 2013, 13, 342-355.
Habashy et al. "Transferrin receptor (CD71) is a marker of poor prognosis in breast cancer and can predict response to tamoxifen." Breast cancer research and treatment 119.2 (2010): 283-293.
Pinnix et al. "Ferroportin and iron regulation in breast cancer progression and prognosis." Science translational medicine 2.43 (2010): 43ra56-43ra56.
Ricolleau et al. "Surface-enhanced laser desorption/ionization time of flight mass spectrometry protein profiling identifies ubiquitin and ferritin light chain as prognostic biomarkers in node-negative breast cancer tumors." Proteomics 6.6 (2006): 1963-1975.
Spangler et al. "A reactivity-based probe of the intracellular labile ferrous iron pool." Nature chemical biology 12.9 (2016): 680-685.
Kalinowski et al. "The evolution of iron chelators for the treatment of iron overload disease and cancer." Pharmacological reviews 57.4 (2005): 547-583.
Merlot et al. "Novel chelators for cancer treatment: where are we now?." Antioxidants & redox signaling 18.8 (2013): 973-1006.
Yu et al., "Thiosemicarbazones from the Old to New: Iron Chelators That Are More Than Just Ribonucleotide Reductase inhibitors," J. Med. Chem., Apr. 30, 2009, 52, 5271-5294.
Lovejoy et al. "Novel second-generation di-2-pyridylketone thiosemicarbazones show synergism with standard chemotherapeutics and demonstrate potent activity against lung cancer xenografts after oral and intravenous administration in vivo." Journal of medicinal chemistry 55.16 (2012): 7230-7244.
Jansson et al. "Di-2-pyridylketone 4, 4-dimethyl-3-thiosemicarbazone (Dp44mT) overcomes multidrug resistance by a hovel mechanism involving the hijacking of lysosomal P-glycoprotein (Pgp)." Journal of Biological Chemistry 290.15 (2015): 9588-9603.
Jansson et al. "The renaissance of polypharmacology in the development of anti-cancer therapeutics: Inhibition of the "Triad of Death" in cancer by Di-2-pyridylketone thiosemicarbazones." Pharmacological research 100 (2015): 255-260.
Wang et al. "Stimulus-responsive prochelators for manipulating cellular metals." Accounts of chemical research 49.11 (2016): 2468-2477.
Chang et al. "Disulfide/thiol switches in thiosemicarbazone ligands for redox-directed iron chelation." Dalton Transactions 42.22 (2013): 7846-7849.
Akam et al. "Intracellular reduction/activation of a disulfide switch in thiosemicarbazone iron chelators." Metallomics 6.10 (2014): 1905-1912.
Pujol et al. "A Sulfur Tripod Glycoconjugate that Releases a High-Affinity Copper Chelator in Hepatocytes." Angewandte Chemie International Edition 51.30 (2012): 7445-7448.
Schafer et al. "Redox environment of the cell as viewed through the redox state of the glutathione disulfide/glutathione couple." Free radical biology and medicine 30.11 (2001): 1191-1212.
Gamcsik et al. "Glutathione levels in human tumors." Biomarkers 17.8 (2012): 671-691.
Lee et al. "Disulfide-cleavage-triggered chemosensors and their biological applications." Chemical reviews 113.7 (2013): 5071-5109.
Lee et al. "Disulfide-based multifunctional conjugates for targeted theranostic drug delivery." Accounts of chemical research 48.11 (2015): 2935-2946.
Ballatori et al. "Glutathione dysregulation and the etiology and progression of human diseases." (2009): 191-214.
Akam "Targeting iron in colon cancer via glycoconjugation of thiosemicarbazone prochelators." Bioconjugate chemistry 27.8 (2016): 1807-1812.
Mertens et al. "Intracellular iron chelation modulates the macrophage iron phenotype with consequences on tumor progression." PLoS One 11.11 (2016): e0166164.
Potůčková et al. "Structure-activity relationships of novel salicylaldehyde isonicotinoyl hydrazone (SIH) analogs: iron chelation, antioxidant and cytotoxic properties." PLoS One 9.11 (2014): e112059.
Soares et al. "Evaluation of thiosemicarbazones and semicarbazones as potential agents anti-Trypanosoma cruzi." Experimental parasitology 129.4 (2011): 381-387.
Potůčková et al. "In vitro characterization of the pharmacological properties of the anti-cancer chelator, Bp4eT, and its phase I metabolites." PloS one 10.10 (2015): e0139929.
Jansson et al. "The iron complex of Dp44mT is redox-active and induces hydroxyl radical formation: an EPR study." Journal of inorganic biochemistry 104.11 (2010): 1224-1228.
Kalyanaraman et al. "Measuring reactive oxygen and nitrogen species with fluorescent probes: challenges and imitations." Free radical biology and medicine 52.1 (2012): 1-6.
Franks et al. "A prochelator with a modular masking group featuring hydrogen peroxide activation with concurrent fluorescent reporting." Chemical Communications 50.77 (2014): 11317-11320.
Charkoudian et al. "Iron prochelator BSIH protects retinal pigment epithelial cells against cell death induced by hydrogen peroxide." Journal of inorganic biochemistry 102.12 (2008): 2130-2135.
Karlsson et al. "What does the commonly used DCF test for oxidative stress really show?." Biochemical Journal 428.2 (2010): 183-190.
Le et al. "The role of iron in cell cycle progression and the proliferation of neoplastic cells." Biochimica et Biophysica Acta (BBA)—Reviews on Cancer 1603.1 (2002): 31-46.
Eriksson et al. "Cell cycle-dependent regulation of mammalian ribonucleotide reductase. The S phase-correlated Increase in subunit M2 is regulated by de novo protein synthesis." Journal of Biological Chemistry 259.19 (1984): 11695-11700.
Cooper et al. "The relationship of intracellular iron chelation to the inhibition and regeneration of human ribonucleotide reductase." Journal of Biological Chemistry 271.34 (1996): 20291-20299.
Eberhard et al. "Chelation of intracellular iron with the antifungal agent ciclopirox olamine induces cell death in eukemia and myeloma cells." Blood, The Journal of the American Society of Hematology 114.14 (2009): 3064-3073.
Aye et al. "Mechanistic studies of semicarbazone triapine targeting human ribonucleotide reductase in vitro and in mammalian cells: tyrosyl radical quenching not involving reactive oxygen species." Journal of Biological Chemistry 287.42 (2012): 35768-35778.
Popović-Bijelić et al. "Ribonucleotide reductase inhibition by metal complexes of Triapine (3-aminopyridine-2-carboxaldehyde thiosemicarbazone): a combined experimental and theoretical study." Journal of inorganic biochemistry 105.11 (2011): 1422-1431.
Macková et al. "Methyl and ethyl ketone analogs of salicylaldehyde isonicotinoyl hydrazone: novel iron chelators with selective antiproliferative action." Chemico-biological interactions 197.2-3 (2012): 69-79.
Pan et al. "Increased GADD153 gene expression during iron chelation-induced apoptosis in Jurkat T-lymphocytes." Biochimica et Biophysica Acta (BBA)—Molecular Cell Research 1691.1 (2004): 41-50.
Regis et al. "Iron regulates T-lymphocyte sensitivity to the IFN-γ/STAT1 signaling pathway in vitro and in vivo." Blood 105.8 (2005): 3214-3221.
Noulsri et al. "Antitumor activity and mechanism of action of the iron chelator, Dp44mT, against leukemic cells." American journal of hematology 84.3 (2009): 170-176.
Ponka, Prem. "Tissue-specific regulation of iron metabolism and heme synthesis: distinct control mechanisms in erythroid cells." Blood, The Journal of the American Society of Hematology 89.1 (1997): 1-25.
Muckenthaler et al. "A red carpet for iron metabolism." Cell 168.3 (2017): 344-361.
Ohta et al. "Erythroid cell differentiation: murine erythroleukemia cell variant with unique pattern of induction by polar compounds." Proceedings of the National Academy of Sciences 73.4 (1976): 1232-1236.

(56) References Cited

OTHER PUBLICATIONS

Marcero et al. "Rapid and sensitive quantitation of heme in hemoglobinized cells." Biotechniques 61.2 (2016): 83-91.
Chan et al. "Regulation of transferrin receptor mRNA expression: distinct regulatory features in erythroid cells." European journal of biochemistry 220.3 (1994): 683-692.
Schranzhofer et al. "Remodeling the regulation of iron metabolism during erythroid differentiation to ensure efficient heme biosynthesis." Blood 107.10 (2006): 4159-4167.
Sheftel et al. "Direct interorganellar transfer of iron from endosome to mitochondrion." Blood, The Journal of the American Society of Hematology 110.1 (2007): 125-132.
Hamdi et al. "Erythroid cell mitochondria receive endosomal iron by a "kiss-and-run" mechanism." Biochimica Et Biophysica Acta (BBA)—Molecular Cell Research 1863.12 (2016): 2859-2867.
Schultz et al. "Iron and porphyrin trafficking in heme biogenesis." Journal of Biological Chemistry 285.35 (2010): 26753-26759.
Sung et al. "Albumin Conjugates of Thiosemicarbazone and Imidazole-2-thione Prochelators: Iron Coordination and Antiproliferative Activity." ChemMedChem 16.18 (2021): 2764-2768.
Jávorfi et al. "Quantitative spectrophotometry using integrating cavities." Journal of Photochemistry and Photobiology B: Biology 82.2 (2006): 127-131.
Ongena et al. "Determining cell number during cell culture using the Scepter cell counter." JoVE (Journal of Visualized Experiments) 45 (2010): e2204.
Papireddy et al., "Antimalarial Activity of Natural and Synthetic Prodiginines," J_ Med. Chem. Jul. 8, 2011, 54, 5296-5306.
Perez-Tomas et al., "New Insights on the Antitumoral Properties of Prodiginines," Curr. Med. Chem. Jul. 1, 2010, 17, 2222-2231.
Regourd et al., "Synthesis and Anti-Cancer Activity of C-Ring-FtmctionaHzed Prodigiosin Analogues," J_ Med. Chem. 2007, 50, 1528-1536.
Diaz et al., "Amido-Functionalised Prodigiosenes: Synthesis and Anticancer Properties," ChemMedChem 2009, 4, 742-745.
Smithen et al., "Investigations regarding the utility of prodigiosenes to treat leukemia," Org. Biomol. Chem. 2013, 11, 62-68.
Melvin et al., "DNA Binding by 4-Methoxypyrrolic Natural Products. Preference for Intercalation at AT Sites by Tambjamine E and Prodigiosin," J_ Org. Chem. Jun. 10, 1999, 64, 6861-6869.
Sessler et al., "Synthesis, Anion-Binding Properties, and In Vitro Anticancer Activity of Prodigiosin Analogues," Angew. Chem., Int. Ed. 2005, 44, 5989-5992.
Davis et al., "Using small molecules to facilitate exchange of bicarbonate and chloride anions cross liposomal membranes," Nat. Chem. Apr. 19, 2009, 1, 138-144.
Busschaert et al., "Small-Molecule Lipid-Bilayer Anion Transporters for Biological Applications," Angew. Chem., Int. Ed. 2013, 52, 1374-1382.
Melvin et al., "Double-Strand DNA Cleavage by Copper-Prodigiosin," J. Am. Chem. Soc. Jan. 6, 2000, 122, 6333-6334.
Melvin et al., "Copper-nuclease efficiency correlates with cytotoxicity for the 4-methoxypyrrolic natural products," J_ Inorg. Biochem. Aug. 14, 2001, 87, 129-135.
Diaz et al., "Chloride anion transport and copper-1nediated I)NA cleavage by C-ring functionalized prodigiosenes," Chem. Commun. Feb. 12, 2007, 2701-2703.
Furstner et al., "Synthesis and Biological Evaluation of Nonylprodigiosin and Macrocyclic Prodigiosin Analogues," ChemBioChem 2001, 2, 706-709.
Melvin et al., "Influence of the A-Ring on the Proton Affinity and Anticancer Properties of the Prodigiosins," Chem. Res. Toxicol. 2002, 15, 734-741.
Zhang et al., "One-pot efficient synthesis of pyrrolylBODIPY dyes from pyrrole and acyl chloride," RSC Advances 2012, 2, 11215-11218.
Zhang et al., "Synthesis of pyrrolyldipyrrinato BF 2 complexes by oxidative nudeophilk substitution of boron dipyrromethene with pyrrole," Org. Biomol. Chem. 2012, 10, 2139-2145.

Park et al., "Zinc and Copper Complexes of Prodigiosin: Implications for Copper-Mediated Double-Strand DNA Cleavage," Org. Lett. 2003, 5, 113-116.
Crawford et al., "Synthesis and Characterization of Fluorescent Pyrrolyldipyrrinato Sn(IV) Complexes," Inorg. Chem. 2011, 50, 8207-8213.
Hong et al., "Syntheses of mono- and diacylated bipyrroles with rich substitution modes and development of a prodigiosin derivative as a fluorescent Zn(11) probe," RSC Adv. 2014, 4, 6133-6140.
Murakami., "Transition-metal Complexes of Pyrrole Pigments. Part VI. Some Bivalent Metal Complexes of 3,3' ,4',4'-Tetrachloro-5,5'-diethoxycarb-onyldipyrromethene," J_ Chem. Soc., Dalton Trans. 1973, 1729-1734.
Smithen et al., "Use of f-BODIPYs as a Protection Strategy for Dipyrrins: Optimization of BF2 Removal," J_ Org. Chem. 2012, 77, 3439-3453.
Wallace et al., "Rational Tetraarylporphyrin Syntheses: Tetraarylporphyrins from the MacDonald Route," J_ Org. Chem. Jul. 14, 1993, 58, 7245-7257.
Garcia-Valverde et al., "Conformational Analysis of a Model Synthetic Prodiginine," J_ Org. Chem. 2012, 77, 6538-6544.
Melvin et al., "Influence of the A-Ring on the Redox and Nuclease Properties of the Prodigiosins: Importance of the Bipyrrole Moiety in Oxidative DNA Cleavage," Chem. Res. Toxicol. 2002, 15, 742-748.
Rastogi et al., "Synthetic prodigiosenes and the influence of C-ring substitution on DNA cleavage, transmembrane chloride transport and basicity," Org. Biomol. Chem. 2013, 11, 3834-3845.
Yu et al. "Straightforward Acid-Catalyzed Synthesis of Pyrrolyldipyrromethenes," Angew. Chem., Int. Ed. 2012, )1, 7688-7691.
Jenkins et al., "Structural studies of C-ring substituted unnatural analogues of prodigiosin" CrystEngComm 2009, 11, 242-245.
Davies, "A New Pulse Endor Technique" E. R., Phys. Lett. A Feb. 2, 1974, 47, 1-2.
Holland et al., "Three-Coordinate Cu(II) Complexes: Structural Models of Trigonal-Planar Type I Copper Protein Active Sites," J_ Am. Chem. Soc. May 10, 1999, 121, 7270-7271.
Holland et al., "A Structural Model of the Type I Copper Protein Active Site: N2S(thiolate)S{thioether) Ligation in a Cu{H) Complex," J_ Am. Chem. Soc. 2000, 122, 6331-6332.
Pap et al. "Tetra-, penta-and hexacoordinate copper (II) complexes with N3 donor isoindoline-based ligands: Characterization and SOD-like activity." Inorganica Chimica Acta 376.1 (2011): 158-169.
Iwaizumi et al. "Correlation between the hyperfine coupling constants of donor nitrogens and the structures of the first coordination sphere in copper complexes as studied by nitrogen-14 ENDOR spectroscopy." Inorganic Chemistry 25.10 (1986): 1546-1550.
Mitrikas et al. "Asymmetric Spin Density Distribution in the Copper (ii) Complex of N-Confused Tetraphenylporphyrin: A Multifrequency Continuous-Wave and Pulse EPR Study." Angewandte Chemie International Edition 44.21 (2005): 3301-3303.
Heinze et al. "Heteroleptic Cu (II) dipyrromethene complexes linked via hydrogen bonds, coordinative bonds, and covalent bonds: probing the coordination environment by electron paramagnetic resonance spectroscopy." Inorganic chemistry 45.6 (2006): 2695-2703.
Bailey et al. "Ethyl Pyrrole-2-Carboxylate: 1H-Pyrrole-2-carboxylic acid, ethyl ester." Organic syntheses 51 (2003): 100-100.
Sheldrick, George M. "A short history of SHELX." Acta Crystallographica Section A: Foundations of Crystallography 64.1 (2008): 112-122.
Macrae et al. "Mercury CSD 2.0—new features for the visualization and investigation of crystal structures." Journal of Applied Crystallography 41.2 (2008): 466-470.
Spek, A. L. J. "Single-crystal structure validation with the program PLATON." Journal of applied crystallography 36.1 (2003): 7-13.
Van der Sluis et al. "BYPASS: an effective method for the refinement of crystal structures containing disordered solvent regions." Acta Crystallographica Section A: Foundations of Crystallography 46.3 (1990): 194-201.

(56) References Cited

OTHER PUBLICATIONS

Astashkin et al. "26.5-40 GHz Ka-band pulsed EPR spectrometer." Concepts in Magnetic Resonance Part B: Magnetic Resonance Engineering: An Educational Journal 29.3 (2006): 125-136.

Humphlett, W. J. "4-(D-arabino-tetrahydroxybutyl)-4-thiazoline-2-thione synthesis of optical isomers and analogs." Carbohydrate Research 7.4 (1968): 431-441.

Humphlett, W. J. "A determination of the structure of 4-(d-arabino-tetrahydroxybutyl)-4-thiazoline-2-thione." Carbohydrate Research 6.1 (1968): 25-33.

Serra et al., "Thiosemicarbazide, a fragment with promising indolamine-2,3-dioxygenase (IDO) inhibition properties," Eur. J.Med. Chem. 82, 2014, 96-105.

Kwok et al., "The iron metabolism of neoplastic cells: Alterations that facilitate proliferation?" Crit. Rev. Oncol. Hemalol. 2002, 42, 65-78.

Yu et al., "Chelators at the cancer coalface: Desferrioxamine to triapine and beyond," Clin. Cancer Res.Dec. 1, 2006, 12, 6876-6883.

Richardson et al. "Cancer cell iron metabolism and the development of potent iron chelators as anti-tumour agents." Biochimica et Biophysica Acta (BBA)—General Subjects 1790.7 (2009): 702-717.

Sutherland et al., "Ubiquitous cell-surface glycoprotein on tumor cells is proliferation-associated receptor for transferrin," Proc. Nall. Acad. Sci. U. S. A. Mar. 17, 1981, 78, 4515-4519.

Kontoghiorghes et al., "Chelators controlling metal metabolism and toxicity pathways: Applications in cancer prevention, diagnosis and treatment," Hemoglobin 2008, 32, 217-227.

\* cited by examiner

Example 1

Example 2

Example 3

Example 4

Example 5

Example 6

Example 7

Example 8

Example 9

Example 10

Example 11

Example 12

Example 13

Example 14

Example 15

Thiosemicarbazone class

Example 16

Example 17

Example 18

Semicarbazone class

Example 19

Example 20

Aroyl Hydrazone class

|  | $IC_{50}$ (μM, 72 h) | | |
| --- | --- | --- | --- |
|  | MDA-MB-231 | MCF-7 | MRC-5 |
| (TC1-S)$_2$ | 4.4 ± 0.7 | 12.3 ± 0.8 | 30 ± 5 |
| (TC3-S)$_2$ | 17.0 ± 0.4 | 48.3 ± 1.2 | 27.3 ± 1.6 |
| (TC5-S)$_2$ | 17 ± 3 | 37 ± 1 | > 300 |
| (TC6-S)$_2$ | 18.1 ± 0.9 | 19.5 ± 1.5 | 29.0 ± 0.6 |
| (AH1-S)$_2$ | 6.7 ± 0.5 | 4.6 ± 0.9 | 20.5 ± 1.0 |
| (AH2-S)$_2$ | 17.1 ± 1.5 | 45.3 ± 2.9 | > 100 |
| (SC2-S)$_2$ | 45 ± 4 | 53 ± 1 | 91 ± 3 |
| TE1 | >200 | >100 | >100 |

Scheme 1

$R_1$ = H, Me ; $R_2$ = H, Ph ; X = S, O

*TC and SC prochelators*

R = H, Me

*AH prochelators*

DISULFIDE-MASKED PRO-CHELATOR COMPOSITIONS AND METHODS OF USE

CROSS-REFERENCES TO RELATED APPLICATIONS

This application is a Continuation-In-Part and claims priority to U.S. patent application Ser. No. 16/632,217, filed Jan. 17, 2020, which is a 371 application of PCT/US18/42458 filed Jul. 17, 2018, which claims priority to U.S. Provisional Patent Application No. 62/533,964, filed Jul. 18, 2017, the specifications of which are incorporated herein in their entirety by reference.

This application is also a Continuation-In-Part and claims priority to U.S. patent application Ser. No. 16/200,286, filed Nov. 26, 2018, which is a continuation-in-part and claims benefit of U.S. patent application Ser. No. 15/345,393, filed Nov. 7, 2016, which is a continuation and claims benefit of U.S. patent application Ser. No. 14/531,634, filed Nov. 3, 2014, now U.S. Pat. No. 9,486,423, which claims benefit of U.S. Provisional Patent Application No. 61/899,262, filed Nov. 3, 2013, the specification(s) of which is/are incorporated herein in their entirety by reference.

U.S. patent application Ser. No. 16/200,286 is also a continuation-in-part and claims benefit of U.S. patent application Ser. No. 16/014,905, filed Jun. 21, 2018, which is a continuation-in-part of PCT Application No. PCT/US16/68061, filed Dec. 21, 2016, which claims benefit of U.S. Provisional Application No. 62/270,246, filed Dec. 21, 2015, the specification(s) of which is/are incorporated herein in their entirety by reference. U.S. patent application Ser. No. 16/014,905 is also a continuation-in-part and claims benefit of Ser. No. 15/345,393, filed Nov. 7, 2016, which is a continuation and claims benefit of U.S. patent application Ser. No. 14/531,634, filed Nov. 3, 2014, now U.S. Pat. No. 9,486,423, which claims benefit of U.S. Provisional Patent Application No. 61/899,262, filed Nov. 3, 2013, the specification(s) of which is/are incorporated herein in their entirety by reference.

STATEMENT REGARDING FEDERALLY SPONSORED RESEARCH OR DEVELOPMENT

This invention was made with government support under Grant No. R01 GM127646, awarded by National Institutes of Health. The government has certain rights in the invention.

FIELD OF THE INVENTION

The present invention relates to chelating compounds, more particularly to pro-chelators that upon activation yield active chelators, such as but not limited to disulfide-masked pro-chelators. The pro-chelators of the present invention may be used for intracellular metal sequestration or for other purposes.

BACKGROUND OF THE INVENTION

The present invention features pro-chelator compositions, e.g., pro-chelator molecules, which upon activation yield an active chelator. For example, a disulfide reduction/activation switch incorporated on thiosemicarbazone scaffolds results in activated iron prochelators. In addition to thiosemicarbazone pro-chelators, the present invention also features several tridentate donor sets including aroyl hydrazones and semicarbazones.

As described in Example 1, the compositions of the present invention have been found to have anti-proliferative effects in certain breast adenocarcinoma cells lines (MCF7 and metastatic MDA-MB-231), and they do not result in the intracellular generation of oxidative stress. Flow cytometry experiments in cultured Jurkat cells indicated that the tested prochelators lead to cell cycle arrest at the $G_{1/0}$ interface and result in induction of apoptosis. Thus, the present invention also features methods of reducing or inhibiting proliferation of cells that are in an abnormal proliferative state (e.g., cancer cells), methods for inducing apoptosis in such cells, methods of treating cancers, methods of treating diseases or conditions associated with metal ion dysregulation, etc.

SUMMARY OF THE INVENTION

The present invention features pro-chelators comprising at least one pro-ligand and a disulfide bond, having the disulfide bond connected to the pro-ligand, and having each pro-ligand comprise at least two donor atoms. In some embodiments, the pro-chelator is selectively reduced within a cell with iron ion dysregulation. The pro-chelator compositions of the present invention may be used for biological purposes, e.g., for intracellular metal ion chelation (e.g., iron chelation).

The present invention also features a method of reducing or inhibiting proliferation of a cell. In some embodiments, the method comprises introducing a pro-chelator of the present invention (e.g., according to Formula I, Formula II, Formula III). The pro-chelator can be activated in the cell yielding an active chelator. The active chelator can chelate metal ions and reduce or inhibit proliferation of the cell. In one embodiment, the cell is a cell with iron dysregulation and the active chelator chelates iron ions. In another embodiment, the cell is proliferating abnormally, and the active chelator chelates iron ions.

The present invention also features a method of treating a clinical condition associated with metal ion dysregulation in a subject in need of said treatment. The method may comprise administering to the subject a therapeutically effective amount of a pro-chelator of the present invention. The pro-chelator is reduced within a cell having a metal ion dysregulation to yield an active chelator that chelates metal ions. Chelation of metal ions by the active chelator within the cell with a metal dysregulation alleviates the clinical condition associated with metal ion dysregulation. In some embodiments, the clinical condition associated with metal ion dysregulation is a cancer.

The present invention also features a method of treating a clinical condition associated with abnormal cell proliferation in a subject in need of said treatment. The method may comprise administering to the subject a therapeutically effective amount of a pro-chelator of the present invention. The pro-chelator is reduced within a cell that proliferates abnormally to yield an active chelator that chelates metal ions. Chelation of metal ions by the active chelator within the cell that proliferates abnormally alleviates the clinical condition associated with abnormal cell proliferation. In some embodiments, the clinical condition associated with abnormal cell proliferation is a cancer.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The features and advantages of the present invention will become apparent from a consideration of the following detailed description presented in connection with the accompanying drawings in which.

DEFINITIONS

Figure 1:
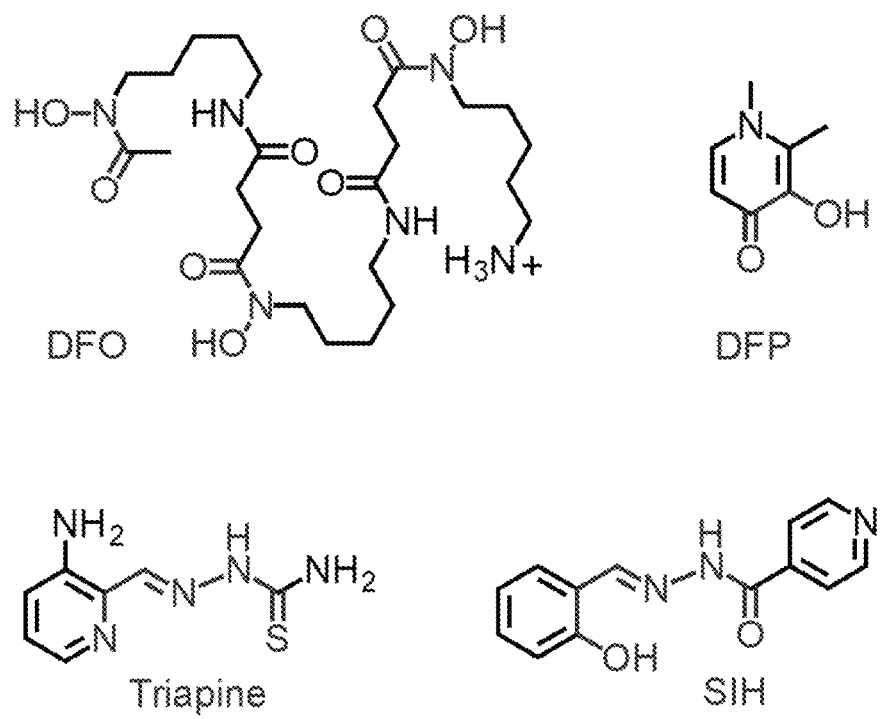
FIG. 1 shows prior art examples of iron-binding units in chelators employed for biomedical applications.

"Donor atoms" refers to atoms which comprise at least one pair of electrons which can be donated to coordinate a metal atom or ion. "Polydentate" refers to a ligand attached to the central atom in a coordination complex by two or more bonds. "Solubilizing" refers to a group which increases or decreases a hydrophilicity of a molecule to increase its solubility in an environment. "Biologically active" refers to a group which is capable of exerting a pharmacological activity on a biological sample.

"Alkyl" refers to a saturated linear monovalent hydrocarbon moiety of one to twelve, typically one to six, carbon atoms or a saturated branched monovalent hydrocarbon moiety of three to twelve, typically three to six, carbon atoms. Exemplary alkyl group include, but are not limited to, methyl, ethyl, n-propyl, 2propyl, tert-butyl, pentyl, and the like.

"Aryl" refers to a monovalent mono-, bi- or tricyclic aromatic hydrocarbon moiety of 6 to 15 ring atoms that is optionally substituted with one or more substituents within the ring structure. When two or more substituents are present in an aryl group, each substituent is independently selected.

The term "heteroaryl" means a monovalent monocyclic or bicyclic aromatic moiety of 5 to 12 ring atoms containing one, two, or three ring heteroatoms selected from N, O, or S, the remaining ring atoms being C. The heteroaryl ring is optionally substituted independently with one or more substituents.

Exemplary heteroaryls include, but are not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like.

"Pharmaceutically acceptable excipient" refers to an excipient that is useful in preparing a pharmaceutical composition that is generally safe and non-toxic. The excipient may be acceptable for veterinary use as well as human pharmaceutical use.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to a pharmacologically substantially inactive derivative of a parent drug molecule that requires biotransformation, either spontaneous or enzymatic, within the organism to release the active drug. Prodrugs are variations or derivatives of the compounds of this invention, which have groups cleavable under metabolic conditions. Prodrugs become the compounds of the invention that are pharmaceutically active in vivo when they undergo solvolysis or reduction or other reaction eliciting activation under physiological conditions or undergo enzymatic processing. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, *Design of Prodrugs*, pp. 7-9, 21-24, Elsevier, Amsterdam 1985 and Silverman, *The Organic Chemistry of Drug Design and Drug Action*, pp. 352-401, Academic Press, San Diego, Calif., 1992). Prodrugs commonly known in the art include acid derivatives that are well known to one skilled in the art, such as, but not limited to, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability. For example, a compound of the invention having free amino, amido, hydroxy or carboxylic groups can be converted into prodrugs. Prodrugs include compounds wherein an amino acid residue, or a polypeptide chain of two or more (e.g., two, three or four) amino acid residues, which are covalently joined through peptide bonds to free amino, hydroxy or carboxylic acid groups of compounds of the invention. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters that are covalently bonded to the above substituents of a compound of the invention through the carbonyl carbon prodrug side chain.

The term "chelator" refers to a compound or a moiety that is capable of coordinating (or binding) a metal ion in a polydentate (e.g., coordination via two or more atoms of moieties) fashion. The terms "pro-chelator" and "prochelators" are used interchangeably herein and refer to a compound or a moiety that is transformed into a chelator following activation via a chemical reaction (e.g., with or by another compound including via redox reaction) or by an enzyme.

The term "anion stabilizing group" refers to a moiety whose presence in the molecule increases the stability of the anion relative to the absence of such a group. One skilled in the art can readily determine whether a substituent or a moiety is an anion stabilizing group, e.g., by determining the increase in the acidity of the resulting compound compared to a corresponding compound in the absence of such group. One can empirically determine the anion stabilization of a particular group by determining the pKa of the compound having the anion stabilizing group and comparing it with the pKa of the corresponding compound in the absence of the anion stabilizing group. Typically, the anion stabilizing compound will have a lower pKa, i.e., it will be more acidic.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P or S) to which it is attached.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "iron ion-overload" (or iron dysregulation) refers to a cell whose iron ion concentration is above the normal iron ion concentration and manifests abnormal clinical condition. The iron ion-overload can be the cause of the clinical condition or it can be a result of the clinical condition. It should be appreciated that the iron ion concentration of a normal cell can vary depending on the type of cells. The terms "iron overload" and "iron ion-overload" are used interchangeably herein and typically refers to the condition of patients presenting systemic iron concentrations that are significantly higher than normal, e.g., the amount of iron concentration in subjects that do not show any observable clinical condition(s). Iron overload can be due to accidental exposure to excessive iron or to genetic conditions that lead to accumulation of iron, such as hemochromatosis, or to conditions that require multiple blood transfusions, such as thalassemia. Thus, a clinical condition associated with the iron overload includes clinical condition in which the iron ion-overload is a cause or the effect of such a clinical condition.

It is believed that cancer cells do not have a significantly higher systemic iron levels in general. However, cancer cells are more susceptible to iron deprivation because they require higher iron levels. Accordingly, in some embodiments of the invention, the method includes treating a cancer patient by administering a therapeutically effective amount of a compound of the invention. In these embodiments, the amount of compound administered is of sufficient amount to cause deprivation of iron in cancer cells to effectively cause apoptosis of cancer cells.

DETAILED DESCRIPTION OF THE INVENTION

The present invention features pro-chelator compositions, e.g., pro-chelator molecules, which upon activation yield active chelators. Pro-chelators of the present invention may comprise a disulfide mask, wherein a reduction/activation switch incorporated in the pro-chelators (e.g., thiosemicarbazone) results in active iron prochelators. The present invention also features several tridentate donor sets including aroyl hydrazones and semicarbazones.

In one embodiment, the present invention features a pro-chelator comprising at least one pro-ligand and a disulfide bond, having the disulfide bond connected to the pro-ligand, and having each pro-ligand comprise at least two donor atoms. In another embodiment, the present invention features a method of preventing iron-deficiency anemia while treating a subject having malignant cells characterized by a reprogrammed iron metabolism. As a non-limiting example, the method may comprise: providing a pro-chelator to a bloodstream of the subject; and transporting the pro-chelator to an intracellular space of a malignant cell of the subject. In preferred embodiments, an active chelator may be selectively released from the pro-chelator by reduction of the disulfide bond within the intracellular space. In additional preferred embodiments, the active chelator may coordinate Fe selectively within the intracellular space to form a metal complex, and not coordinate Fe in the bloodstream of the subject. In further preferred embodiments, the selective coordination of Fe may be effective for treating the malignant cells without causing iron-deficiency anemia.

According to some embodiments, the pro-chelator may comprise two pro-ligands, connected by the disulfide bond. According to some other embodiments, the pro-chelator may comprise one pro-ligand and a solubilizing or biologically active moiety, connected by the disulfide bond. In some preferred embodiments, the pro-chelator may be activated to transform each pro-ligand to an active bidentate, tridentate, or polydentate chelator. As a non-limiting example, the pro-chelator may be activated by reduction of the disulfide bond.

In other embodiments, each active chelator may comprise a semicarbazone, a thiosemicarbazone, a hydrazone, or a thiohydrazone moiety. In still other embodiments, each active chelator may comprise an iminic position, and may comprise an electron-withdrawing group at the iminic position. In yet other embodiments, each active chelator may be configured to coordinate Fe to form a metal complex. In even another embodiment, the metal complex has a $Fe^{III}/Fe^{II}$ potential of about −200 to 200 mV compared to a Normal Hydrogen Electrode (NHE). In other embodiments, the metal complex has a $Fe^{III}/Fe^{II}$ potential of about −1000 to 1000, −900 to 900, −800 to 800, −700 to 700, −600 to 600, −500 to 500, −400 to 400, −300 to 300, −100 to 100, −50 to 50, or −10 to 10 mV, compared to a Normal Hydrogen Electrode (NHE).

In another embodiment, the pro-chelator may comprise a structure according to Formula II, Formula III, Formula IV, or Formula V.

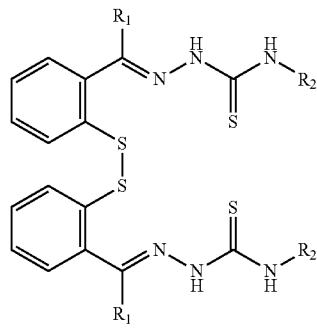

(TC1-S)$_2$ R = H, R$_2$ = Ph
(TC3-S)$_2$ R$_1$ = H, R$_2$ = H
(TC5-S)$_2$ R$_1$ = Me, R$_2$ = Ph
(TC6-S)$_2$ R$_1$ = Me, R$_2$ = H

Formula II

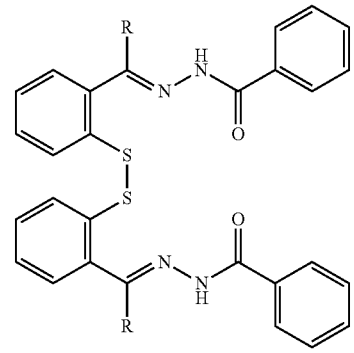

(AH1-S)$_2$ R = H
(AH2-S)$_2$ R = Me

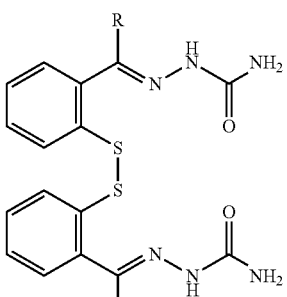

(SC1-S)$_2$ R = H
(SC2-S)$_2$ R = Me

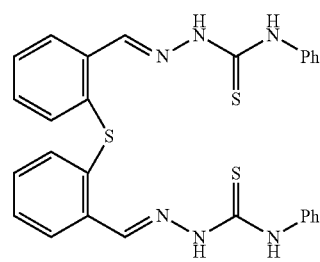

TE1

(TC1-S)₂ R₁ = H, R₂ = Ph
(TC3-S)₂ R₁ = H, R₂ = H
(TC5-S)₂ R₁ = Me, R₂ = Ph
(TC6-S)₂ R₁ = Me, R₂ = H (AH1-S)₂ R = H
(AH2-S)₂ R = Me (SC1-S)₂ R = H
(SC2-S)₂ R = Me

TE1

Formula III

Formula IV

Formula V

In an embodiment, the present invention may feature a pro-chelator according to Formula II or Formula III, wherein R is H, alkyl, aryl, or a derivative thereof. In some embodiments, R may be trifluoromethyl. In other embodiments, the pro-chelator may be redox-activated. In further embodiments, the pro-chelator may be selectively reduced within a cell with iron ion dysregulation.

In another embodiment, the present invention may feature a pro-chelator according to Formula IV.

In one embodiment, if $X_1$=O, then $R_1$=Ph, pyridyl, p-$CF_3$-Ph, p-$NO_2$-Ph, $CCl_3$, or $CF_3$; $X_2$=H, alkyl, alkoxy, halo, $CF_3$, or $NO_2$; $R_2$=H, alkyl, aryl, or substituted aryl; and $R_3$=H, alkyl, aryl, or substituted aryl. In an alternative embodiment, if $X_1$=S, then $R_1$=Ph, pyridyl, p-$CF_3$-Ph, p-$NO_2$-Ph, $CCl_3$, or $CF_3$; $X_2$=H, alkyl, alkoxy, halo, $CF_3$, or $NO_2$; $R_2$=alkyl, aryl, or substituted aryl; and $R_3$=alkyl, aryl, or substituted aryl.

In still another embodiment, the present invention may feature a pro-chelator according to Formula V. In some embodiments, $X_1$=O or S; $R_1$=Ph, pyridyl, p-$CF_3$-Ph, p-$NO_2$-Ph, $CCl_3$, or $CF_3$; $X_2$=H, alkyl, alkoxy, halo, $CF_3$, or $NO_2$; and $X_3$=H, alkyl, alkoxy, halo, $CF_3$, or $NO_2$.

In one embodiment, the present invention features a method of reducing or inhibiting proliferation of a cell. As a non-limiting example, the method may comprise introducing a pro-chelator, wherein the pro-chelator is activated by reduction of the disulfide bond in an intracellular space of the cell to transform each pro-ligand to an active bidentate, tridentate, or polydentate chelator, wherein each active chelator coordinates metal ions and reduces or inhibits proliferation of the cell. In another embodiment, the cell may be a cell with iron dysregulation or a cell that is proliferating abnormally. In still another embodiment, the active chelator may coordinate iron ions.

In some embodiments, the present invention may feature a method of treating a clinical condition associated with metal ion dysregulation in a subject in need of said treatment. As a non-limiting example, the method may comprise administering to the subject a therapeutically effective amount of a pro-chelator, wherein said pro-chelator is activated by reduction of the disulfide bond in an intracellular space of the cell to transform each pro-ligand to an active bidentate, tridentate, or polydentate chelator that coordinates metal ions, whereby coordination of metal ions by said active chelators alleviates said clinical condition associated with metal ion dysregulation. In one embodiment, the clinical condition associated with metal ion dysregulation may be cancer.

In still other embodiments, the present invention may feature a method of treating a clinical condition associated with abnormal cell proliferation in a subject in need of said treatment. As a non-limiting example, the method may comprise: administering to the subject a therapeutically effective amount of a pro-chelator, wherein said pro-chelator is activated by reduction of the disulfide bond in an intracellular space of the cell to transform each pro-ligand to an active bidentate, tridentate, or polydentate chelator that coordinates metal ions, whereby coordination of metal ions by said active chelators alleviates said clinical condition associated with abnormal cell proliferation. In some embodiments, the clinical condition associated with abnormal cell proliferation may be cancer.

Formula 1 features a pro-chelator of the present invention (a thiosemicarbazone pro-chelator). In some embodiments, $R_1$ is H or methyl or a derivative thereof. In some embodiments, $R_2$ is H, methyl, phenyl, other aryl or heteroaryl, or a derivative thereof. In some embodiments, $R_1$ is H and $R_2$ is phenyl. In some embodiments, $R_1$ is H and $R_2$ is H. In some embodiments, $R_1$ is methyl and $R_2$ is phenyl. In some embodiments, $R_1$ is methyl and $R_2$ is H. In some embodiments, $R_1$ is H and $R_2$ is methyl. In some embodiments, $R_1$ is methyl and $R_2$ is an aryl or heteroaryl.

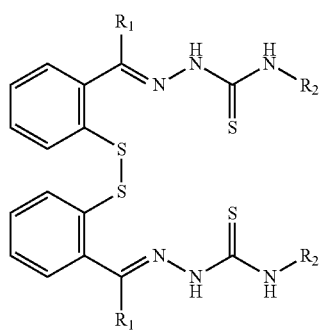

(TC1-S)$_2$ R$_1$ = H, R$_2$ = Ph
(TC3-S)$_2$ R$_1$ = H, R$_2$ = H
(TC5-S)$_2$ R$_1$ = Me, R$_2$ = Ph
(TC6-S)$_2$ R$_1$ = Me, R$_2$ = H

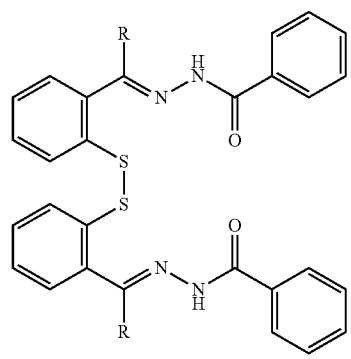

(AH1-S)$_2$ R = H
(AH2-S)$_2$ R = Me

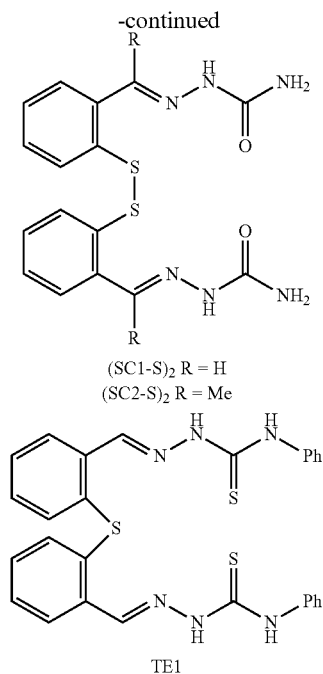

(SC1-S)$_2$ R = H
(SC2-S)$_2$ R = Me

TE1

Figure 3A:
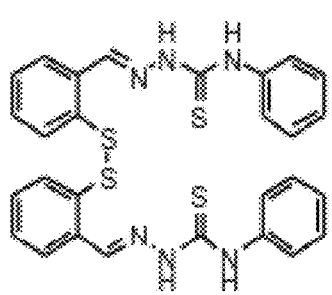
FIG. 3A shows non-limiting examples of thiosemicarbazone pro-chelators.
Figure 3A:
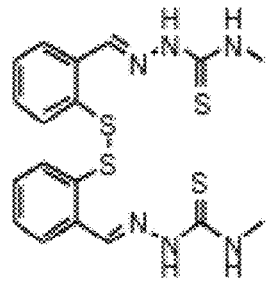
Figure 3A:
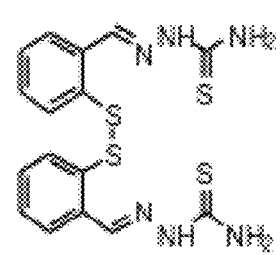
Figure 3A:
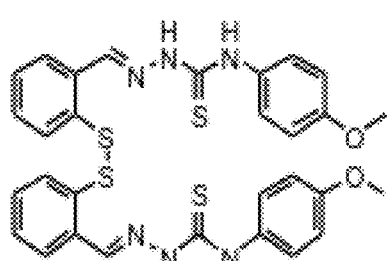
Figure 3A:
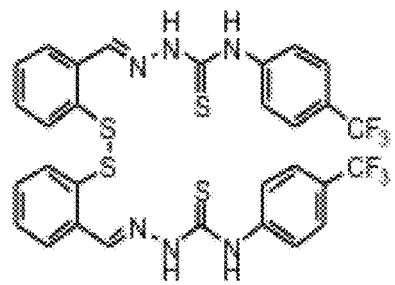
Figure 3A:
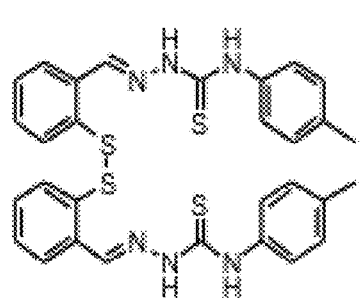
Figure 3A:
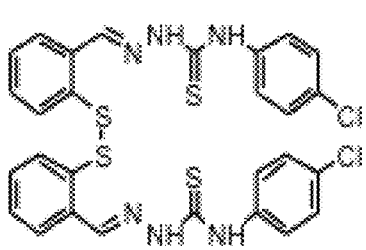
Figure 3A:
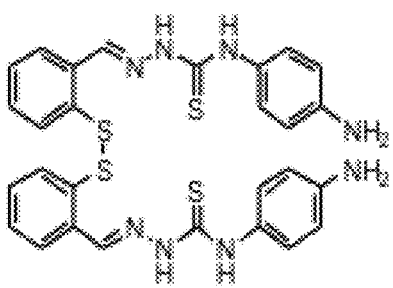
Figure 3A:
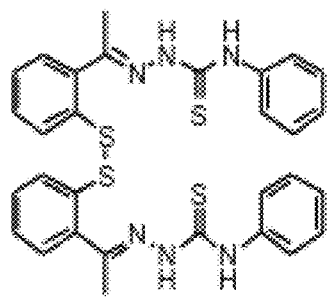
Figure 3A:
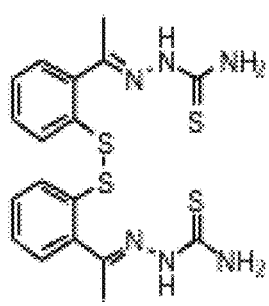
Figure 3A:
Figure 3A:
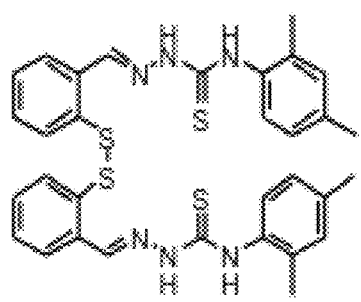
Figure 3A:
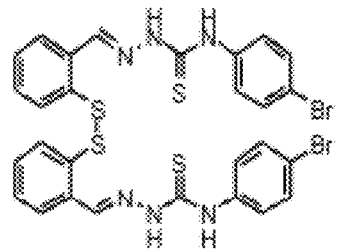
Figure 3A:
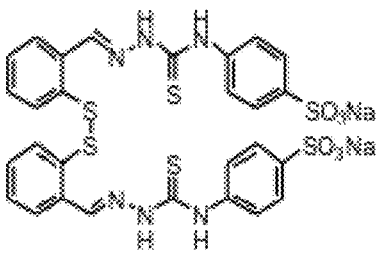
Figure 3A:
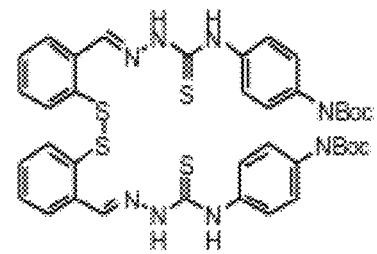

FIG. 3A shows specific examples of Formula 1 (thiosemicarbazone pro-chelator compositions). For example, Example Compound 1 is formed when $R_1$ is H and $R_2$ is phenyl. Example Compound 2 is formed when $R_1$ is H and $R_2$ is methyl. Example Compound 3 is formed when $R_1$ is H and $R_2$ is H. Example Compound 4, Example Compound 5, Example Compound 6, Example Compound 7, Example Compound 8, Example Compound 11, Example Compound 12, Example Compound 13, Example Compound 14, and Example Compound 15 are formed when $R_1$ is H and $R_2$ is a phenyl derivative. Example Compound 9 is formed when $R_1$ is methyl and $R_2$ is a phenyl derivative. Example Compound 10 is formed when $R_1$ is methyl and $R_2$ is H.

Formula II shows semicarbazone pro-chelators. In some embodiments, R is H or methyl or a derivative thereof.

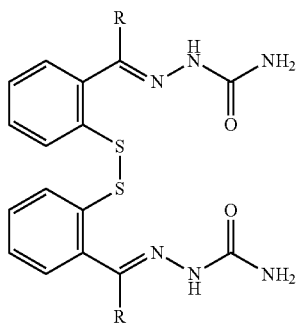

Figure 3B:
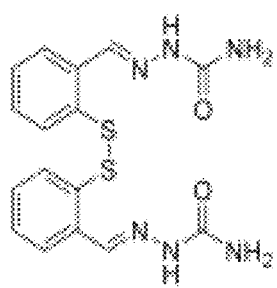
FIG. 3B shows non-limiting examples of semicarbazone pro-chelators.
Figure 3B:
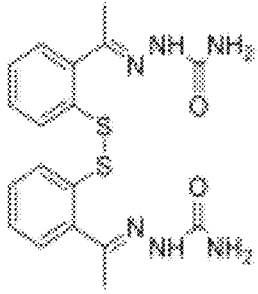
Figure 3B:
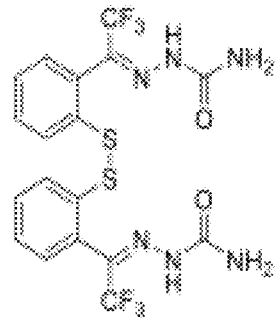

FIG. 3B shows specific examples of Formula II (semicarbazone pro-chelator compositions). For example, Example Compound 16 is formed when R is H. Example Compound 17 is formed when R is methyl. Example Compound 18 is formed when R is a methyl derivative, specifically trifluoromethyl.

Formula III shows aroyl hydrazone pro-chelators. In some embodiments, R is H or methyl or a derivative thereof.

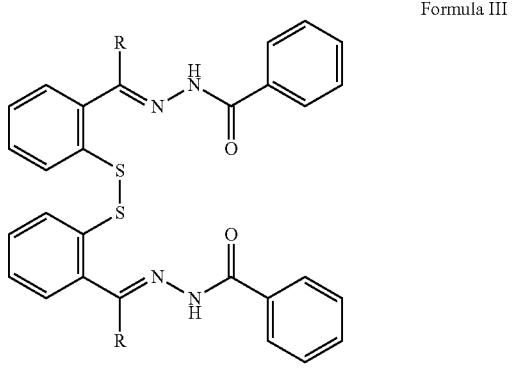

Formula III

Figure 3C:
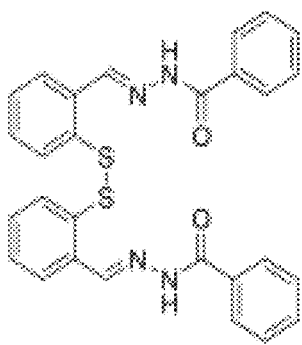
FIG. 3C shows non-limiting examples of aroyl hydrazone pro-chelators.
Figure 3C:
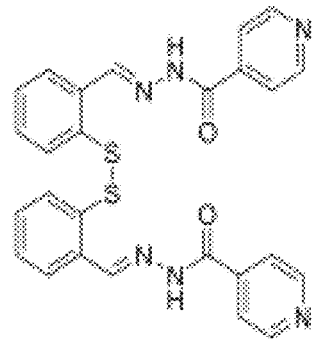

FIG. 3C shows specific examples of Formula III (aroyl hydrazone pro-chelator compositions). For example, Example Compound 19 is formed when R is H. Example Compound 20 is formed when R is methyl and the terminal phenyl groups comprise nitrogen.

The pro-chelator compositions of the present invention may be used for biological purposes, e.g., for intracellular metal ion chelation (e.g., iron chelation). The present invention also features methods of reducing or inhibiting proliferation of cells that are in an abnormal proliferative state (e.g., cancer cells) using the pro-chelator compositions of the present invention. The present invention also features methods for inducing apoptosis in cells that are in an abnormal proliferative state (e.g., cancer cells) using the pro-chelator compositions of the present invention. The present invention also features methods of treating diseases associated with metal ion dysregulation using the pro-chelator compositions of the present invention. The present invention also features methods of treating diseases associated with cells in an abnormal proliferative state (e.g., cancers) using the pro-chelator compositions of the present invention. The present invention also features methods of synthesis of pro-chelators of the present invention.

The present invention also includes pharmaceutical compositions comprising at least one compound of the invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

Non-limiting examples of pharmaceutical carriers and their formulations are described in Remington: *The Science and Practice of Pharmacy* 1995, edited by E. W. Martin, Mack Publishing Company, 19th edition, Easton, Pa.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation.

EXAMPLE 1

Rapidly dividing malignant cells are characterized by a reprogrammed iron metabolism, which enhances intracellular iron availability through an altered expression of several key proteins for iron homeostasis. Correspondingly, the expression levels of transferrin receptors, ferroportin and ferritin have been identified as prognostic markers in breast cancer patients. At a molecular level, reactivity-based fluorescent probes of intracellular iron have shown recently that the labile iron pool is larger in several cancer cell lines when compared to non-malignant ones. As such, high-affinity scavengers (chelators) can be employed to target the increased iron needs of cancer cells for the development of antineoplastic agents. The scaffolds of chelators studied in this context vary substantially (see FIG. 1): from hexadentate hydroxamate-based siderophores (e.g., desferrioxamine aka DFO) to bidentate deferiprone (DFP) to tridentate thiosemicarbazones (e.g., Triapine) and aroylhydrazones (e.g., salicyl isonicotinoyl hydrazone aka SIH).

Thiosemicarbazones were found to have growth inhibition effects in sarcomas. Since then, numerous thiosemicarbazones and hydrazones have been studied for their antineoplastic effects in vitro and in animal models.

Furthermore, Triapine has been investigated in several clinical trials. More recently, new classes of thiosemicarbazones were investigated for their antineoplastic effects. These studies produced highly potent compounds such as di-2-pyridylketone 4,4-dimethyl-3-thiosemicarbazone (Dp44mT) and di-2-pyridylketone 4-cyclohexyl-4-methyl-3-thiosemicarbazone (DpC), which proved effective in vitro and in vivo through oral and intravenous administration, and demonstrated the potential to overcome multidrug resistance, as well as some of the limitations of Triapine including methemoglobin formation. DpC has entered clinical trials in 2016.

Within the study of metal-binding pharmaceuticals, prochelation strategies are being pursued to minimize off-target toxicity through inclusion of structural motifs that render the chelator inactive until triggered by disease-specific conditions. Examples of this approach include prochelators that are activated by intracellular enzymes, under oxidative stress conditions, and by reduction of disulfide bonds.

The disulfide reduction/activation approach employs disulfide bonds as redox-sensitive switches that are triggered upon cell entry by the high concentrations of cytosolic thiols with respect to the extracellular milieu. For instance, the intracellular concentrations of reduced glutathione (5-11 mM) are orders of magnitude greater than those in the extracellular space and blood plasma (<5 µM). As such, disulfide linkages are employed extensively in prodrug and chemosensor design, and recent theranostic systems have allowed visualization of selective disulfide-based drug release in vivo. In addition, malignant tissue contains higher levels of glutathione when compared to the neighboring normal tissue, therefore disulfide switches are particularly attractive for the design of antiproliferative prochelator systems.

Figure 2:
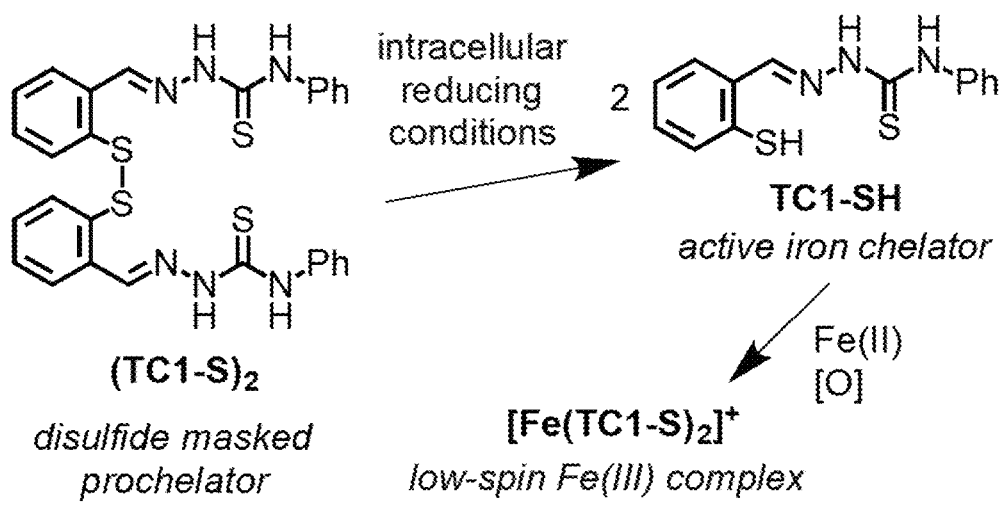
FIG. 2 shows an example of a scheme for reduction/activation of a disulfide switch in thiosemicarbazone pro-chelator $(TC1-S)_2$.

Inventors have previously shown that a disulfide bond can be employed to mask a sulfur donor within tridentate thiosemicarbazone chelators (see FIG. 2). The resulting disulfide-based prochelators do not coordinate metal ions in neutral aqueous solutions, whereas the thiolates generated upon intracellular reduction are high-affinity chelators. In the case of prochelator $(TC1-S)_2$ (FIG. 2), intracellular reduction and iron binding lead to the formation of a low-spin ferric complex that is not redox active. Inventors have also utilized disulfide switches as linkers in glycoconjugate prochelator systems targeting the overexpression of glucose transporters in colon cancer cells. Furthermore, disulfide-based thiosemicarbazone prochelators have the potential to alter iron trafficking and distribution in the tumor microenvironment through their effects on the iron metabolism of tumor-associated macrophages.

The present invention features a disulfide-based prochelation design to aroyl hydrazone and semicarbazone scaffolds. The present invention also features the introduction of a methyl substituent at the iminic carbon in the new prototypes and in the original thiosemicarbazone framework. The present invention also describes intracellular effects of the corresponding chelators, which feature both (S, N, S) and (S, N, O) donor sets, with respect to redox behavior, cell cycle, toxicity and cell death.

Synthesis: The prochelators described herein fall into three classes of metal-binding scaffolds: the thiosemicarbazones (TC compounds), the aroyl hydrazones (AH compounds) and the semicarbazones (SC compounds). The selected compounds allowed comparison of binding groups with (S,N,S) and (S,N,O) donor sets, as well as different functional groups (e.g., aroyl hydrazones vs. semicarbazones within the (S,N,O) binding units). In addition, methyl hydrazone analogs were included because studies on SIH and related high-affinity hydrazone chelators indicated that these derivatives are more stable with respect to hydrolytic degradation.

Thioether TE1 was synthesized as a control analog of prochelator (TC1-S)$_2$ lacking the disulfide bond. TE1 does not bind iron in physiologically relevant conditions and cannot be reduced by intracellular thiols to produce an iron-binding species.

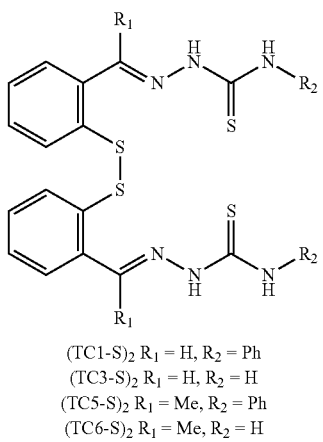

(TC1-S)$_2$ R$_1$ = H, R$_2$ = Ph
(TC3-S)$_2$ R$_1$ = H, R$_2$ = H
(TC5-S)$_2$ R$_1$ = Me, R$_2$ = Ph
(TC6-S)$_2$ R$_1$ = Me, R$_2$ = H

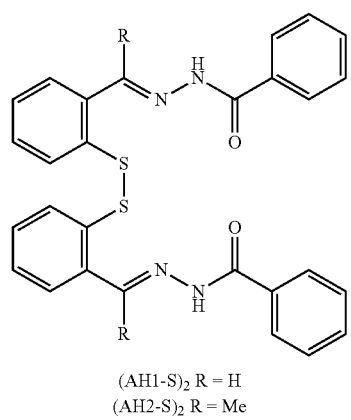

(AH1-S)$_2$ R = H
(AH2-S)$_2$ R = Me

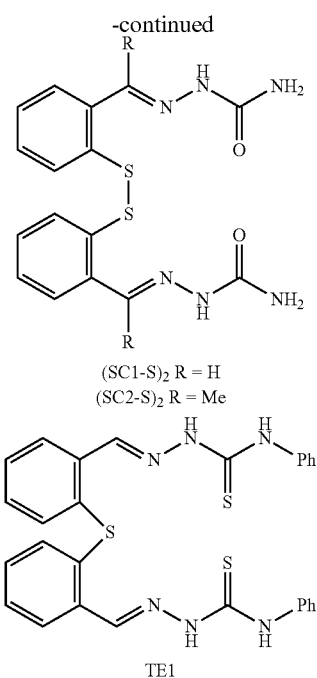

(SC1-S)$_2$ R = H
(SC2-S)$_2$ R = Me

TE1

Figure 8:
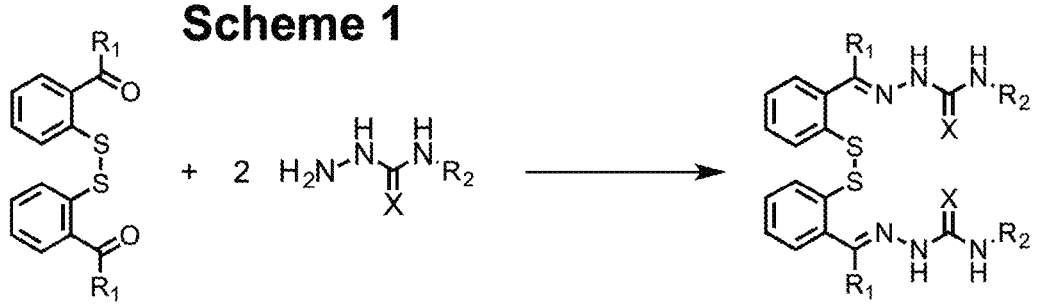
FIG. 8 shows Scheme 1, which is a non-limiting example of synthesis of disulfide-based prochelators via condensation of a thiosemicarbazide, semicarbazide, or hydrazide with a 2,2'-dithiodibenzyl dicarbonyl precursor.
Figure 8:
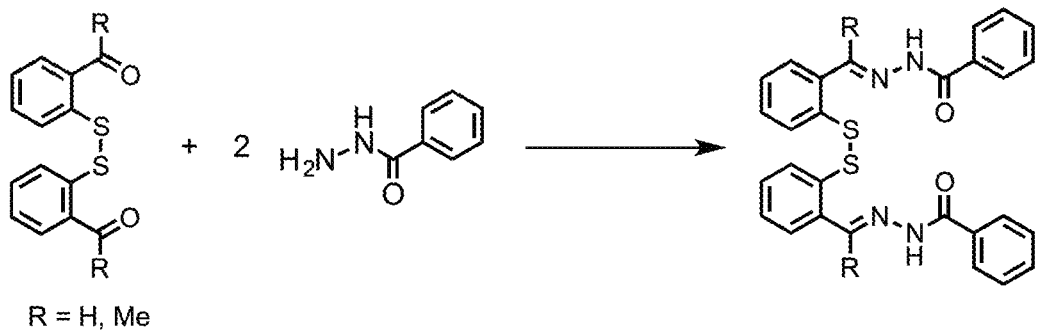

The disulfide-based prochelators were synthesized via Schiff-base condensation reactions between a 2,2'-dithiodibenzyl aldehyde or ketone and a thiosemicarbazide, semicarbazide, or aroylhydrazide (FIG. 8). Details are described below.

Without wishing to limit the present invention to any theory or mechanism, it is believed that an advantage in the purification of the compounds is the solubility difference between the starting materials and the products of the condensation reactions. Although the starting materials are soluble in refluxing alcohols (e.g., methanol, ethanol, isopropanol), the disulfide prochelators generally precipitate from the reaction mixtures.

Antiproliferative activity: The assessment of the antiproliferative activity of the compounds focused on breast cancer because its association to an altered metabolism of iron is well documented.

Figures 4, 5:
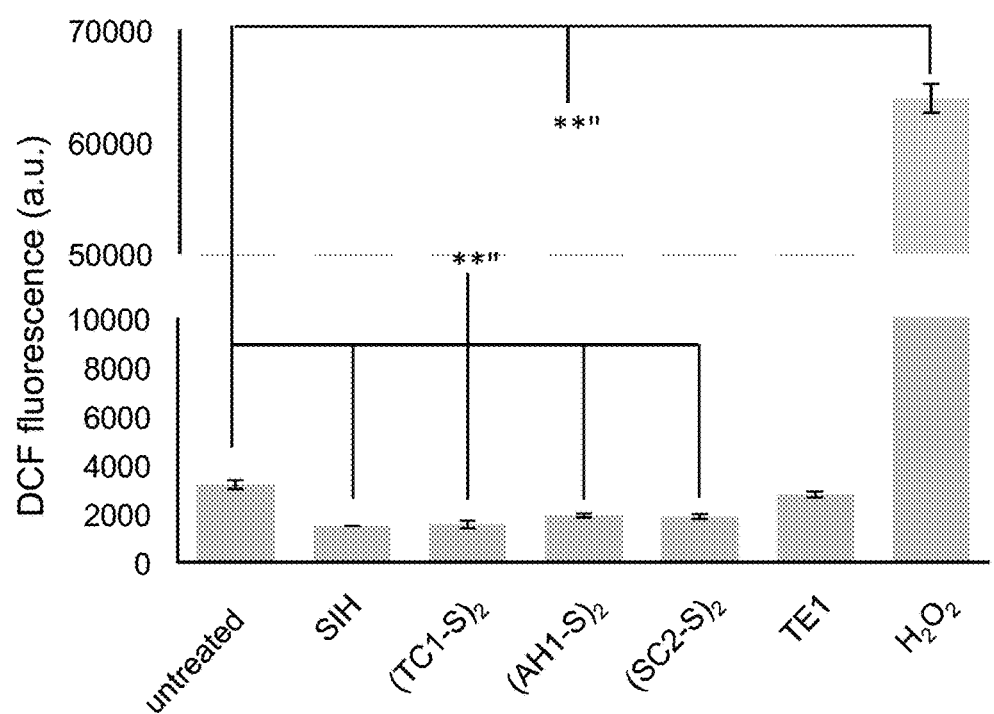
FIG. 4 shows IC50 values for disulfide pro-chelator compositions in the cancer cell lines MDA-MB-231 and MCF-7 and the normal cell line MRC5 after 72-hour incubations with indicated compound. Values were determined using standard MTT assay.
FIG. 5 shows an assessment of intracellular generation of ROS upon incubation with selected pro-chelators. MDA-MB-231 cells were treated with the indicated compounds (50 µM, 2 h), washed, treated with $DCFH_2$-DA (30 µM, 30 min) in PBS, and then analyzed by flow cytometry. Hydrogen peroxide is used as a positive control and SIH as a negative control. Values are presented as mean±SDM (n=3), ** $p<0.01$.

The prochelators were tested in breast adenocarcinomas cell lines MCF-7 (ATCC® HTB-22™) and MDA-MB-231 (ATCC® HTB-26™) as well as in the normal lung fibroblast cell line MRC-5 (ATCC® CCL-171™) using standard MTT assay protocols (FIG. 4).

The antiproliferative activity of the thiosemicarbazone and hydrazone-based disulfide-masked prochelators in cancer cell lines fall within a relatively narrow range, with IC$_{50}$ values mostly ranging from 4 to 50 μM. In the normal fibroblasts, which are typically less sensitive to iron sequestration and present a less reducing environment compared to malignant cells, IC$_{50}$ values were consistently higher than 20 μM and up to more than 100 μM for (AH2-S)$_2$ and (TC5-S)$_2$.

Within the tested panel, it was observed that the semicarbazone (SC2-S)$_2$ presented the highest IC$_{50}$ values. This observation is in line with previous studies showing that semicarbazones typically bind iron with lower affinity and have lower antiproliferative activity as compared to their thiosemicarbazone analogues. Confirming the requirement for intracellular activation and iron binding, the thioether control TE1 did not affect cell viability across all concentrations tested (up to 200 μM).

Inventors have previously shown that the exposure of cultured cells to prochelator $(TC1-S)_2$ leads to iron sequestration and intracellular formation of a low-spin Fe(III) complex. This ferric species is not susceptible to intracellular redox cycling and therefore does not elicit catalytic generation of reactive oxygen species (ROS).

Investigation of intracellular ROS generation: The ability of the disulfide prochelators to induce oxidative stress intracellularly was tested using 2',7'-dichlorodihydrofluorescein diacetate ($DCFH_2$-DA) as a fluorogenic probe. $DCFH_2$-DA, which is hydrolyzed to $DCFH_2$ and trapped intracellularly upon action of esterases, reacts with several ROS/RNS species (e.g., hydroxyl radical, peroxynitrite) to produce the fluorescent dichlorofluorescein (DCF) dye. Hydrogen peroxide (used as the positive control in this assay) does not react directly with $DCFH_2$, but its intracellular metal-mediated decomposition produces the detected ROS/RNS species.

Treatment of MDA-MB-231 breast adenocarcinoma cells with high-affinity chelator SIH (50 μM, 2 h) resulted in suppression of inherent ROS as demonstrated by a significant decrease of DCF fluorescence compared to the untreated control (FIG. 5). This behavior is well documented and SIH is in fact employed to protect cells against metal-mediated oxidative stress. For a selection of prochelators featuring one compound of each family of binding units, it was found that treatment of MDA-MB-231 cells (50 μM, 2 h) also results in a decrease of ROS/RNS levels compared to the untreated control. Conversely, treatment with thioether TE1, which lacks metal-binding affinity, does not result in suppression of basal ROS/RNS concentrations. The antioxidant behavior of the prochelators can therefore be ascribed to metal sequestration, which excludes Fe(II) ions from Fenton chemistry, rather than to radical/ROS scavenging reactivity by their organic framework.

Because the positive control ($H_2O_2$) showed a response that is an order of magnitude higher than that of the untreated control, it was concluded that at the tested concentrations and treatment time, the prochelators described herein in Example 1 do not result in induction of oxidative stress. Rather, as observed for SIH and several analogs, the disulfide-masked prochelators protect against metal-mediated intracellular oxidative stress as measured by $DCFH_2$-DA.

Effects on cell cycle progression: Iron chelation often causes cell cycle arrest at the $G_1/S$ interface, as cells display lower DNA biosynthetic activity and cannot progress through the cell cycle. Although the decreased availability of iron affects several cellular processes, the $G_1/S$ arrest has been attributed, at least in part, to the ability of chelators to decrease the activity of ribonucleotide reductase (RNR), an enzyme that is critical for DNA synthesis. Inventors have previously shown that treatment of cultured Jurkat lymphocyte cells with prochelator $(TC1-S)_2$ results in decreased intracellular levels of active RNR as measured by electron paramagnetic resonance (EPR) spectroscopy. The effects of a selection of prochelators of the present invention on cell cycle progression in the same cell line were investigated. As in the redox activity assays (vide supra), high-affinity chelator SIH was employed as a positive control.

Figure 6:
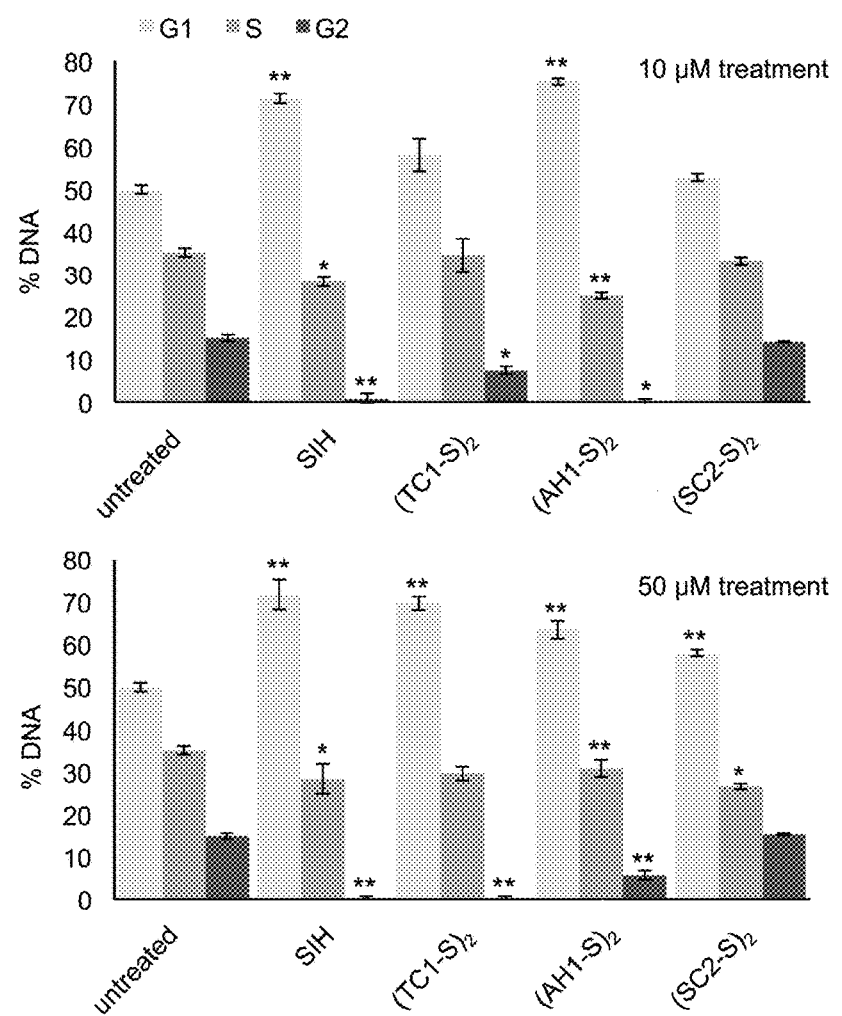
FIG. 6 shows effects of pro-chelators on cell cycle in cultured Jurkat cells. Cells were treated with the compounds (10 or 50 µM, 12 h), harvested, fixed, pelleted and then treated with RNAse and propidium iodide (0.5 mg/mL and 40 µg/mL, respectively, 30 min) prior to analysis by flow cytometry. Values are presented as mean±SDM (n=3), * $p<0.05$ and ** $p<0.01$.

Cell cycle distributions in Jurkat cells were tested after 10 and 50 μM treatment and 12-hour incubations (FIG. 6). At 10 μM, SIH resulted in arrest at the $G_1/S$ interface, with accumulation of $G_{0/1}$ compared to the untreated control. At this concentration, treatment with $(AH1-S)_2$ resulted in $G_{1/0}$ accumulation as significant as that for SIH. This accumulation of cells in the $G_{1/0}$ phase is accompanied by statistically significant depletion of cells in the S phase, with $(AH1-S)_2$ being more effective than SIH (FIG. 6, top panel). Compound $(SC1-S)_2$ also led to significant accumulation of cells in $G_{1/0}$ phase, whereas the other systems did not cause statistically significant changes in this assay. At higher concentrations (50 μM), however, all the prochelators have similar impact on cell cycle, with $G_{1/0}$ accumulation and S depletion being statistically significant in all cases (FIG. 6, bottom panel). These data indicate that all the tested prochelators have effects on cell cycle that are consistent with iron sequestration.

Effects on cell death: Apoptosis is an important form of programmed cell death that is often implicated as the pathway of chelation-induced cytotoxicity. Iron chelators such as DFO, as well as several aroylhydrazones and thiosemicarbazones, initiate the apoptotic pathway of cell death. In the context of this analysis of the biological activity of disulfide-based prochelators, their effects on cell death were investigated using propidium iodide (PI) and a fluorescent analogue of Annexin V (AnnV) as probes for apoptotic markers.

Figure 7:
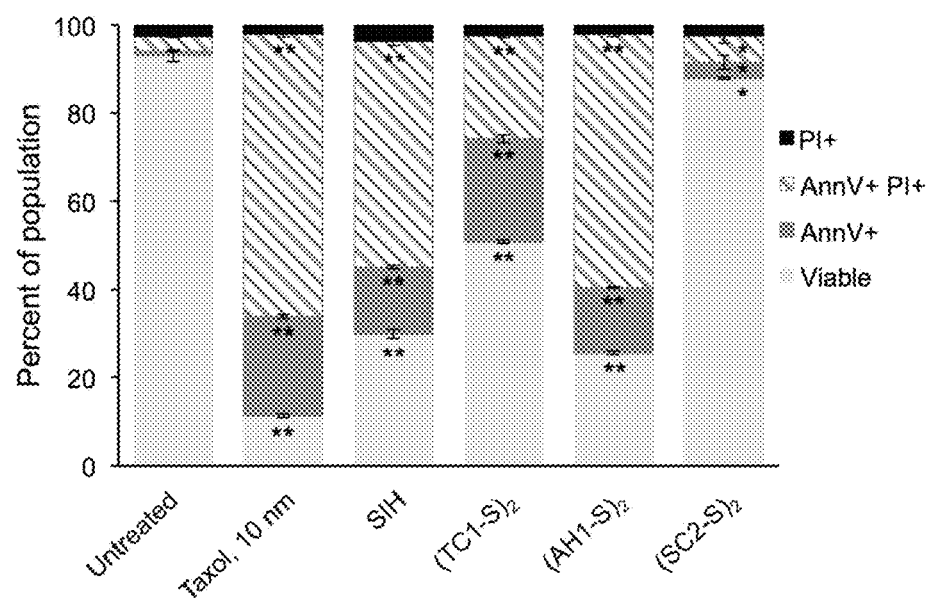
FIG. 7 shows an investigation of cell death in the presence of disulfide-based pro-chelators. Jurkat cells were incubated with the tested compounds (20 µM, 48 h) or vehicle only (DMSO, untreated control). Following treatment with FTIC-Annexin V (AnnV) and propidium iodide (PI), the cells were analyzed by flow cytometry. Values are presented as mean±SDM (n=3), * $p<0.05$ and ** $p<0.01$.

The extent of apoptosis in Jurkat cells were assessed after treatment with prochelators of the present invention for 48 hours (FIG. 7). Potent antineoplastic agent taxol (paclitaxel) was used as a positive control known to induce apoptosis. Tridentate chelator SIH was included as a comparison leading to iron sequestration with no need for intracellular activation. For all tested prochelators, 48-hour treatments resulted in a decrease in viable cells compared to the untreated control. This observation is accompanied by a significant increase in populations that stain positive for AnnV only (termed apoptotic) or AnnV and PI (termed late-apoptotic). Within the prochelator series, $(AH1-S)_2$ was as effective as SIH at inducing apoptosis. The thiosemicarbazone-based prochelator $(TC1-S)_2$ is less effective and the semicarbazone analogue $(SC1-S)_2$ is the least potent of all the compounds tested. These results are consistent with the antiproliferative activity of this series of disulfide-masked prochelators as assessed by colorimetric assays as well as their efficacy in halting cell cycle progression (vide supra). For the thioether control compound TE1, which cannot be reductively activated to sequester intracellular iron, no statistically significant changes were observed in any of the populations (viable, apoptotic, etc.) compared to the untreated control, further validating the reduction/activation pathway as well as the necessity of iron scavenging to induce toxicity.

The induction of apoptosis in Jurkat cells by disulfide-masked prochelators is concentration- and time-dependent, and an increase in AnnV+/PI+ populations was observed with longer incubations or higher concentrations. None of the treatments resulted in significant populations that stained positive for PI only (less than 4% of the population in all cases), ruling out necrosis as a pathway of cell death. In fact, iron scavengers are known to suppress Fe-mediated necrosis that results from Fenton reactions and ROS generation. The lack of a significant necrotic population is in line with the fact that prochelators of the present invention suppress basal ROS levels (vide supra).

Collectively, and in agreement with the $IC_{50}$ values (FIG. 4), the data from cell cycle and cell death assays indicate that aroyl hydrazone $(AH1-S)_2$ and thiosemicarbazone $(TC1-S)_2$ are more effective than semicarbazone $(SC1-S)_2$ as antiproliferative prochelators.

Synthesis of disulfide prochelators: $(TC1-S)_2$, and $(TC3-S)_2$ were synthesized according to reported procedures. The other prochelators were synthesized via condensation of a thiosemicarbazide, semicarbazide, or hydrazide with a 2,2'-dithiodibenzyl dialdehyde or methyldiketone (see FIG. 8).

For example, (TC5-S)$_2$ was synthesized as follows: 1'-(disulfanediylbis(2,1-phenylene))diethanone (150 mg, 0.49 mmol) was suspended in ethanolic HCl (4 mL, 0.12 mM) and was heated to reflux for 30 minutes and 4-phenyl thiosemicarbazide (150 mg, 0.86 mmol) was then added as a solid. The reaction mixture was allowed to reflux for 3 hours. Upon cooling, the resulting precipitate was isolated by filtration, washed with water and dried under vacuum (152 mg, 77% yield). $^1$H NMR (500 MHz, DMSO-d$_6$) δ 11.05 (s, 1H), 10.03 (s, 1H), 7.82 (dd, J=8.1, 1.1 Hz, 1H), 7.70 (ddd, J=9.8, 8.1, 1.1 Hz, 3H), 7.40 (dtd, J=32.2, 7.4, 1.4 Hz, 3H), 7.30-7.23 (m, 2H), 7.13 (tt, J=7.0, 1.1 Hz, 1H), 2.48 (s, 3H). $^{13}$C NMR (126 MHz, DMSO-de) δ 176.42, 149.39, 139.08, 137.44, 135.38, 130.20, 129.802, 128.734, 127.04, 126.79, 125.35, 123.69, 17.11. HRMS m/z [M+Na]$^+$ calculated for C$_{30}$H$_{28}$NS$_4$Na 623.11560; found, 623.11488.

(TC6-S)$_2$ was synthesized as follows: 1'-(disulfanediylbis(2,1-phenylene))diethanone (150 mg, 0.49 mmol) was suspended in ethanolic HCl (7.5 mL, 0.12 mM) and heated to reflux for 30 minutes. Thiosemicarbazide (180 mg, 1.97 mmol) was then added to the reaction flask as a solid and the mixture was allowed to reflux for 3 hours. Upon cooling to room temperature, the precipitate was isolated by filtration, washed with water then dried under vacuum (210 mg, 95% yield). $^1$H NMR (500 MHz, DMSO-d$_6$) δ 10.62 (s, 1H), 8.43 (s, 1H), 7.72-7.67 (m, 1H), 7.64 (dd, J=7.7, 1.3 Hz, 1H), 7.56-7.51 (m, 1H), 7.36 (dtd, J=29.9, 7.6, 1.2 Hz, 2H), 2.40 (s, 3H). $^{13}$C NMR (126 MHz, DMSO-de) δ 179.59, 148.93, 137.63, 135.37, 130.01, 129.63, 126.95, 126.86, 17.05. HRMS m/z [M+Na]$^+$ calculated for C$_{18}$H$_{20}$NS$_4$Na, 471.05300; found, 471.05281.

(AH1-S)$_2$ was synthesized as follows: 2,2'-dithiobenzyldialdehyde (235 mg, 0.86 mmol) was combined with benzhydrazide (256 mg, 1.88 mmol) in ethanol (5 mL) and brought to reflux to dissolve the starting materials. The reaction progress was monitored by TLC. Upon completion, a white solid was collected by filtration, washed with ethanol (3×6 mL) and dried under vacuum (333 mg, 76%). $^1$H NMR (500 MHz, DMSO-d$_6$) δ 12.07 (s, 1H), 8.92 (s, 1H), 7.96 (d, J=7.4 Hz, 2H), 7.89 (d, J=6.9 Hz, 1H), 7.65 (dd, J=27.8, 7.3 Hz, 2H), 7.56 (t, J=7.5 Hz, 3H), 7.43 (p, J=7.0 Hz, 2H). $^{13}$C NMR (126 MHz, DMSO-d$_6$) δ 163.49, 145.90, 135.74, 134.02, 133.66, 132.35, 130.88, 129.86, 128.97, 128.78, 128.45, 128.14, 110.01. HRMS m/z [M+H]$^+$ calculated for C$_{28}$H$_{23}$N$_4$O$_2$S$_2$, 511.12624; found 511.12565; m/z [M+Na]$^+$ calculated for C$_{28}$H$_{22}$N$_4$O$_2$S$_2$Na, 533.10819; found 533.10752.

(AH2-S)$_2$ was synthesized as follows: 1'-(disulfanediylbis(2,1-phenylene))diethanone (37 mg, 0.12 mmol) was suspended in ethanolic HCl (5 mL, 0.12 mM) and was heated to reflux for 30 minutes to dissolve the starting material. Benzhydrazide (42 mg, 0.31 mmol) was then added to the reaction flask as a solid and the solution was allowed to reflux for 3 hours. The resulting precipitate was isolated by vacuum filtration, washed with water, and then dried under vacuum (35 mg, 53% yield). $^1$H NMR (500 MHz, DMSO-d$_6$) δ 9.76 (s, 1H), 8.16 (dd, J=7.8, 1.4 Hz, 1H), 7.82 (dd, J=8.3, 1.4 Hz, 1H), 7.65 (dd, J=8.2, 1.1 Hz, 1H), 7.59-7.55 (m, 1H), 7.55-7.48 (m, 1H), 7.45 (ddt, J=8.2, 6.7, 1.2 Hz, 1H), 7.41 (ddd, J=7.7, 7.3, 1.2 Hz, 2H), 2.70 (s, 3H). $^{13}$C NMR (126 MHz, DMSO-d$_6$) δ 200.03, 166.40, 138.96, 134.73, 133.83, 132.93, 131.49, 128.74, 127.38, 126.45, 125.81, 28.01. HRMS m/z [M+H]$^+$ calculated for C$_{30}$H$_{27}$N$_4$O$_2$S$_2$, 539.15754; found 539.15801; m/z [M+Na]$^+$ calculated for C$_{30}$H$_{26}$N$_4$O$_2$S$_2$Na, 561.13949; found 561.13960.

(SC1-S)$_2$ was synthesized as follows: 2,2'-dithiobenzyldialdehyde (267 mg, 0.97 mmol) was combined with semicarbazide hydrochloride (325 mg, 2.92 mmol) in ethanol (2 mL) and brought to reflux to dissolve the starting materials. The reaction progress was monitored by TLC. Upon completion, an off-white solid was collected by filtration, washed with ethanol (3×4 mL) and dried under vacuum (322 mg, 98%). $^1$H NMR (500 MHz, DMSO-d$_6$) δ 10.49 (s, 1H), 8.30 (s, 1H), 7.96-7.90 (m, 1H), 7.62-7.56 (m, 1H), 7.38-7.32 (m, 2H), 6.48 (s, 2H). $^{13}$C NMR (126 MHz, DMSO-d$_6$) δ 156.86, 137.62, 134.24, 129.91, 129.55, 128.60, 128.33. HRMS m/z [M+Na]$^+$ calculated for C$_{16}$H$_{16}$N$_6$O$_2$S$_2$Na, 411.06738; found 411.06697.

(SC2-S)$_2$ was synthesized as follows: 1'-(disulfanediylbis(2,1-phenylene)) diethanone (100 mg, 0.33 mmol) was combined with semicarbazide hydrochloride (110 mg, 0.99 mmol) in ethanol (2 mL) and brought to reflux. The reaction progress was monitored by TLC. An off-white product was collected by filtration, washed with ethanol (3×4 mL) and dried under vacuum (20 mg, 15%). $^1$H NMR (500 MHz, DMSO-d$_6$) δ 9.65 (s, 1H), 7.65 (dd, J=8.0, 1.3 Hz, 1H), 7.56 (dd, J=7.6, 1.5 Hz, 1H), 7.36-7.26 (m, 2H), 6.40 (s, 2H), 2.28 (s, 3H). $^{13}$C NMR (126 MHz, DMSO-d$_6$) δ 157.35, 144.98, 138.04, 129.36, 129.05, 126.75, 126.53. HRMS m/z [M+H]$^+$ calculated for C$_{18}$H$_{21}$N$_6$O$_2$S$_2$, 417.11674; found 417.11630; m/z [M+Na]$^+$ calculated for C$_{18}$H$_{20}$N$_6$O$_2$S$_2$Na, 439.09868; found 439.09826.

Cytotoxicity assays: MTT (3-(4,5-dimethylthiazol-2-yl)-2,5-diphenyltetrazolium bromide) viability assays were conducted as previously described.[22] Cells were seeded at 4000 cells per well for MCF-7, at 10,000 cells per well for MRC-5 or at 700 cells per well for MDA-MB-231 and allowed to attach for 24 h. Test compounds dissolved in DMSO were diluted in EMEM to the specified concentration with final DMSO concentration limited to 0.1% v/v. Cells were incubated in the presence of the test compounds for 72 h, then the MTT solution (4 mg/mL, 10 µL) was added to each well and incubated for 4 h. Following media removal, DMSO (100 ʇL) was added to each well to dissolve the purple formazan crystals and the plates were incubated for an additional 30 minutes. Absorption at 560 nm was recorded and data were analyzed using logarithmic fits (Origin®) to obtain IC$_{50}$ values. Each experiment was conducted in triplicate, and values are given as mean±SDM.

Detection of Intracellular ROS: Solutions of the fluorescent probe DCFH$_2$-DA (Invitrogen) were prepared in DMSO, aliquoted in single-use doses and stored at −20° C. MDA-MB-231 cells were seeded in 6-well plates at a density of 1.0×10$^5$ cells/mL (2.0×10$^5$ cells/well) and allowed to incubate overnight.

The growth media were then removed, and the adherent cells were treated for 2 hours with the test compounds in phenol-red free EMEM (0.1% DMSO was used to solubilize the compounds). The positive control (H$_2$O$_2$) was diluted in PBS and cells were exposed to this solution for 10 minutes. After incubation, the cells were washed with PBS and then treated with warm PBS containing DCFH$_2$-DA (30 µM) for 20 min. After removal of the probe solution, the cells were washed with PBS (×2) and detached using trypsin-EDTA (3 min). The cell suspension was diluted with growth media (2 mL) and centrifuged at 2000 rpm for 10 minutes. The resulting cell pellet was then suspended in PBS (500 µL), stored on ice, and analyzed by flow cytometry within one hour.

Cell cycle analysis: MDA-MB-231 cells were seeded at 0.2 million cells per well (in EMEM supplemented with 0.1 mg/mL human holo-transferrin) in 6-well plates and allowed to adhere overnight.

Media were removed and solutions containing test compounds were added (final DMSO concentration 0.1% v/v) and cells were incubated for the specified time. Media were then collected, cells washed with PBS (1 mL) and then detached by addition of 0.25% trypsin-EDTA (0.4 mL) followed by a 3-minute incubation. After addition of EMEM (1 mL), the cell suspension was centrifuged at 125×g for 15 minutes. Media were discarded, and cells were fixed by addition of ice-cold 70% ethanol (2 mL) and stored in a freezer at −20° C. overnight (and no longer than one week). Cells were spun at 2000 rpm for 20 minutes, and the resulting pellet was suspended in PBS (0.3 mL) and treated with RNAse and propidium iodide (0.5 mg/mL and 40 µg/mL respectively, 30 min), placed on ice and analyzed by flow cytometry within one hour.

Apoptosis assays: Jurkat cells were grown to 1.5 million cells/mL, then centrifuged and suspended in fresh RPMI medium at 0.5 million cells/mL. Cells were then treated with either test compounds dissolved in DMSO or DMSO alone for control samples (final DMSO concentration 0.1% v/v). Cells were incubated for the specified time and then aliquots of 1 million cells were centrifuged. The pellets were suspended in binding buffer (10 mM HEPES with 150 mM NaCl, 5 mM KCl, 1 mM $MgCl_2$, and 1.8 mM $CaCl_2$, pH 7.4) containing 2 µg/mL FITC-Annexin V (0.3 mL) and solutions were incubated in the dark at room temperature for 10 minutes. Propidium iodide was added prior to analysis at a final concentration of 1 µg/mL.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A metal pro-chelator comprising at least one pro-ligand and a disulfide bond, wherein the disulfide bond is connected to an aromatic ring of the pro-ligand at an ortho position, and wherein each pro-ligand comprises at least two donor atoms; wherein the metal pro-chelator excludes formulations according to:

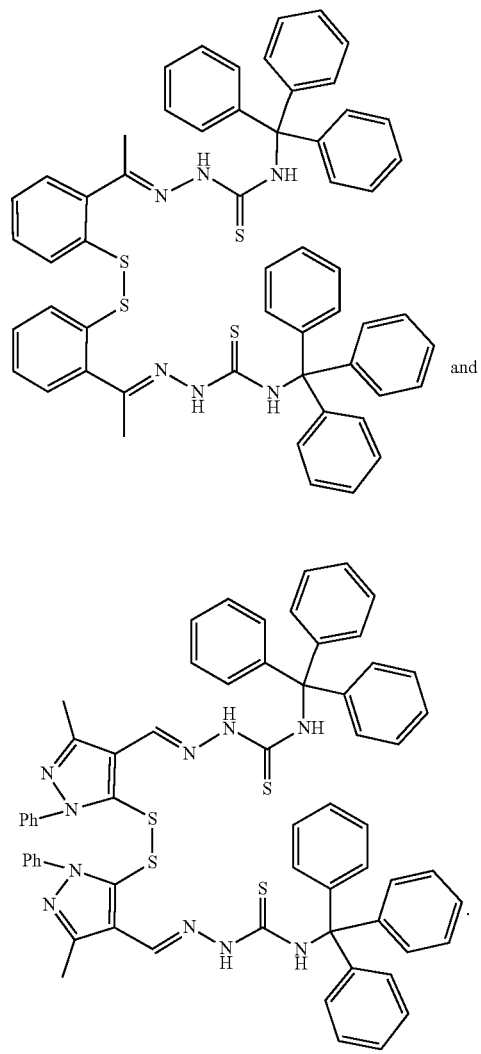

and

2. The pro-chelator of claim 1, wherein the pro-chelator comprises two pro-ligands, connected by the disulfide bond.

3. The pro-chelator of claim 1, wherein the pro-chelator comprises one pro-ligand and a solubilizing or biologically active moiety, connected by the disulfide bond.

4. The pro-chelator of claim 1, wherein the pro-chelator is activated to transform each pro-ligand to an active bidentate, tridentate, or polydentate chelator.

5. The pro-chelator of claim 4, wherein the pro-chelator is activated by reduction of the disulfide bond.

6. The pro-chelator of claim 4, wherein each active chelator comprises a semicarbazone, a thiosemicarbazone, a hydrazone, or a thiohydrazone moiety.

7. The pro-chelator of claim 4, wherein each active chelator comprises an iminic position, and comprises an electron-withdrawing group at the iminic position.

8. The pro-chelator of claim 4, wherein each active chelator is configured to coordinate Fe to form a metal complex.

9. The pro-chelator of claim 1, wherein the pro-chelator comprises a structure according to Formula II, Formula III, Formula IV, or Formula V;

Formula II

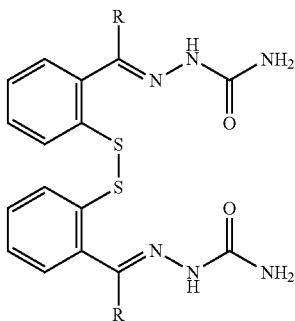

wherein R is H, alkyl, trifluoromethyl, aryl, or a derivative thereof;

Formula III

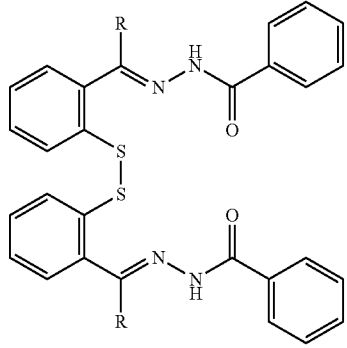

wherein R is H, alkyl, aryl or a derivative thereof;

Formula IV

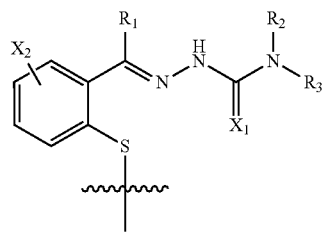

wherein:
if $X_1=O$,
then $R_1$=Ph, pyridyl, p-CF$_3$-Ph, p-NO$_2$-Ph, CCl$_3$, or CF$_3$;
$X_2$=H, alkyl, alkoxy, halo, CF$_3$, or NO$_2$;
$R_2$=H, alkyl, aryl, or substituted aryl; and
$R_3$=H, alkyl, aryl, or substituted aryl;
or if $X_1$=S,
then $R_1$=Ph, pyridyl, p-CF$_3$-Ph, p-NO$_2$-Ph, CCl$_3$, or CF$_3$;
$X_2$=H, alkyl, alkoxy, halo, CF$_3$, or NO$_2$;
$R_2$=alkyl, aryl, or substituted aryl; and
$R_3$=alkyl, aryl, or substituted aryl;

Formula V

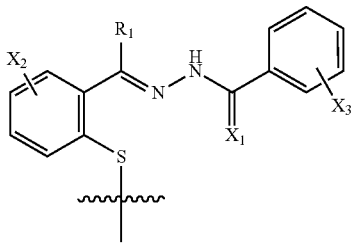

wherein: $X_1$=O, or S;
$R_1$=Ph, pyridyl, p-CF$_3$-Ph, p-NO$_2$-Ph, CCl$_3$, or CF3;
$X_2$=H, alkyl, alkoxy, halo, CF$_3$, or NO$_2$; and
$X_3$=H, alkyl, alkoxy, halo, CF$_3$, or NO$_2$.

10. A pro-chelator according to Formula III, wherein R is H, alkyl, aryl or a derivative thereof Formula III

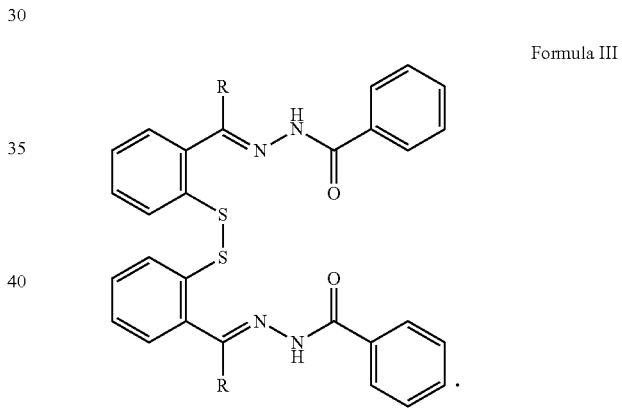

11. The pro-chelator of claim 10, wherein the pro-chelator is redox-activated.

* * * * *